United States Patent [19]
Snyder et al.

[11] Patent Number: 6,103,872
[45] Date of Patent: Aug. 15, 2000

[54] CAPON: A PROTEIN ASSOCIATED WITH NEURONAL NITRIC OXIDE SYNTHASE

[75] Inventors: Solomon H. Snyder; Samie R. Jaffrey, both of Baltimore, Md.

[73] Assignee: The Johns Hopkins University, Baltimore, Md.

[21] Appl. No.: 09/010,998

[22] Filed: Jan. 22, 1998

[51] Int. Cl.[7] .............................. C07K 7/06; C07K 7/08; C07K 14/47
[52] U.S. Cl. ..................... 530/350; 530/326; 530/327; 530/328
[58] Field of Search ................................. 530/300, 324, 530/325, 326, 327, 328, 350

[56] References Cited

PUBLICATIONS

Jaffrey et al. "PIN: An Associated Protein Inhibitor of Neuronal Nitric Oxide Synthase" Science vol. 274, Nov. 1, 1996, pp. 774–777.

Brenman et al. "Interaction of nitric oxide synthase with the postsynaptic density protein PSD–95 and alphal–syntrophin mediated ny PDZ domains" Cell, vol. 84, Mar. 8, 1996, pp. 757–767.

Samie R. Jaffrey et al. "CAPON: A Protein Asociated with Neuronal Nitric Oxide Synthase that Regulates its Interactions with PSD95" Neuron, vol. 20, 115–124 Jan. 1998.

*Primary Examiner*—Robert A. Schwartzman
*Attorney, Agent, or Firm*—Banner & Witcoff, Ltd.

[57] ABSTRACT

Nitric oxide (NO) produced by neuronal nitric oxide synthase (nNOS) is important for N-methyl-D-aspartate (NMDA) receptor-dependent neurotransmitter release, neurotoxicity, and cyclic-GMP elevations. The coupling of NMDA receptor-mediated calcium influx and nNOS activation is postulated to be due to a physical coupling of the receptor and the enzyme by an intermediary adaptor protein PSD95, through a unique PDZ-PDZ domain interaction between PSD95 and nNOS. Here we report the identification of a novel nNOS associated protein, CAPON, which is highly enriched in brain and has numerous colocalizations with nNOS. CAPON interacts with the NNOS PDZ domain through its C-terminus. CAPON competes with PSD95 for interaction with nNOS, and overexpression of CAPON results in a loss of PSD95/nNOS complexes in transfected cells. CAPON influences nNOS by regulating its ability to associate with PSD95/NMDA receptor complexes.

23 Claims, 9 Drawing Sheets

(1 of 9 Drawing Sheet(s) Filed in Color)

FIG. 1B

```
  1        MPSKTKYNLV  DDGHDLRIPL  HNEDAFQHGI  SFEAKYVGSL
 41        DVPRPNSRVE  IVAAMRRIRY  EFKAKNIKKK  KVSIMYSVDG
 81        VKVILKKKKK  KKEWTWDESK  MLVMQDPIYR  IFYVSHDSQD
121        LKIFSYIARD  GASNIFRCNV  FKSKKKSQAM  RIVRTVGQAF
161        EVCHKLSLQH  TQQNADGQED  GESERNSDGS  GDPGROLTGA
201        ERVSTATAEE  TDIDAVEVPL  PGNDILEFSR  GVTDLDAIGK
241        DGGSHIDTTV  SPHPQEPMLA  ASPRMLLPSS  SSSKPPGLGT
281        GTPLSTHHQM  QLLQQLLQQQ  QQQTQVAVAQ  VHLLKDQLAA
321        EAAARLEAQA  RVHQLLLONK  DMLQHISLLV  KQVQELELKL
hCAPON EST                                     KQVQELELKL
361        SGQSTMGSQD  SLLEITFRSG  ALPVLCESTT  PKPEDLHSPL
hCAPON EST SGQNAMGSQD  SLLEITFRSG  ALPVLCDPTT  PKPEDLHSPP
401        LGAGLADFAH  PVGSPLGRRD  CLVKLECFRF  LPAEDNOPMA
hCAPON EST LGAGLADFAH  PAGSPLGRRD  CLVKLECFRF  LPPEDTPPPA
441        QGEPLLGGLE  LIKFRESGIA  SEYESNTDES  EERDSWSQEE
hCAPON EST QGEALLGGLE  LIKFRESGIA  SEYESNTDES  EERDSWSQEE
481        LPRLLNVLQR  QELGDSLDDE  IAV
hCAPON EST LPRLLNVLQR  QELGDGLDDE  IAV
```

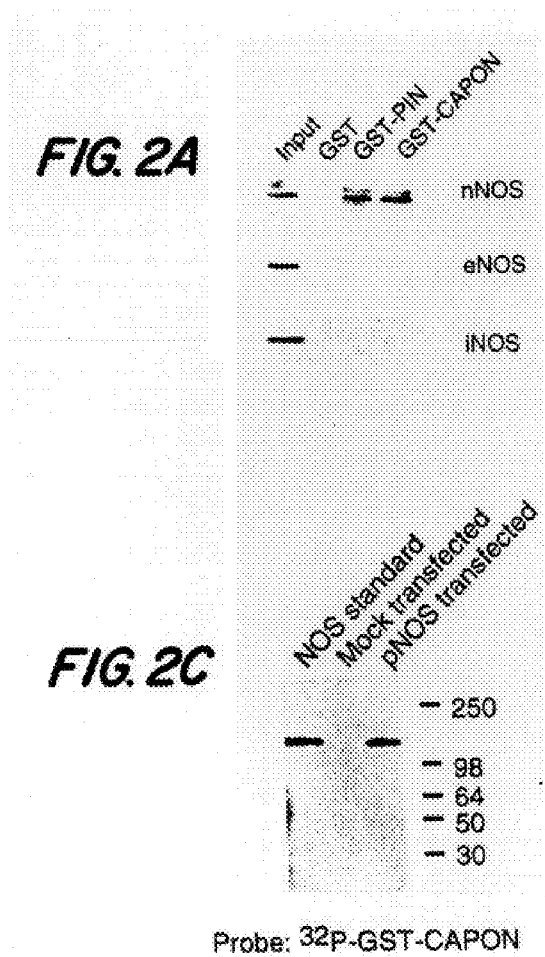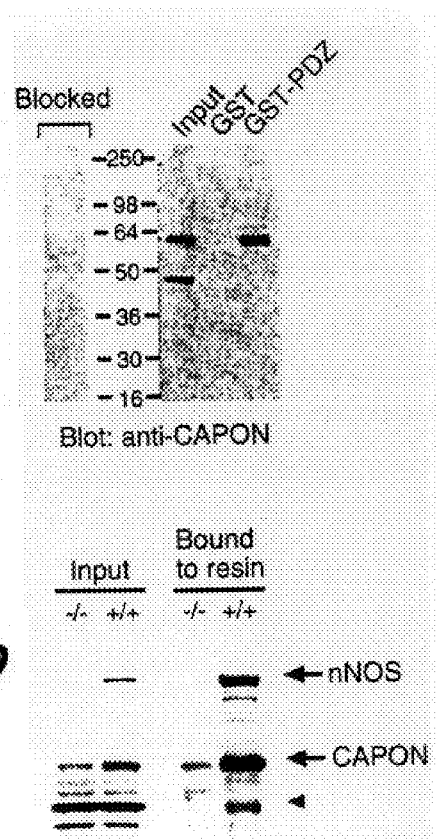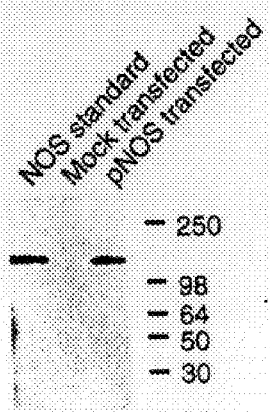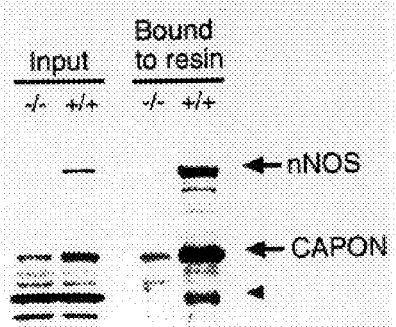
FIG. 2A
FIG. 2B
FIG. 2C
FIG. 2D

FIG. 4A
| nNOS residues | | Reporter |
|---|---|---|
| 1-377 | | + |
| 20-245 | | + |
| 1-160 | | + |
| 1-100 | | + |
| 40-160 | | − |
| 130-232 | | − |
| 163-245 | | − |
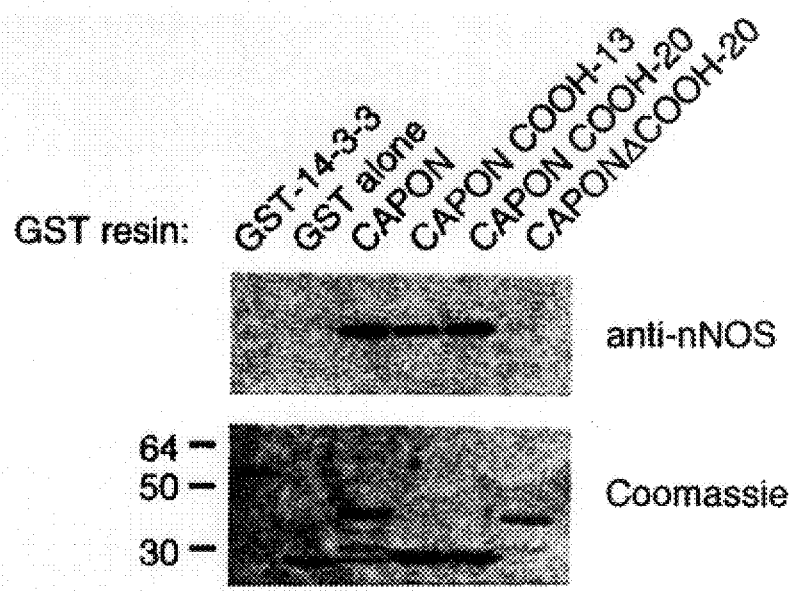
FIG. 4B
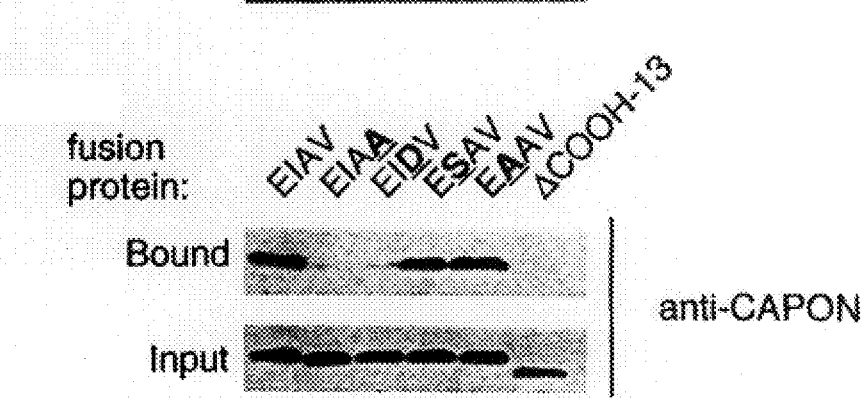
FIG. 4C Model of PSD95/nNOS Regulation by CAPON

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2826 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
GAATTCGGCA CGAGCCGGGT CGTGCGCGCC GAGCTCGGGA TCCGGCTCCC AGTCTAGCCC      60

CGCTTCGGGC CGTGCGCCCT TTGCTCGGCG TCCGGCTCCG GGGCTCCGCG CCACCCGCTC     120

CCGCCTGCCC GGCCGCCTGG CCGCCTCCCC GTAGTCAGAG CGCGGCCACC GAGCTGCTCG     180

CGCCAGCCGC ATCCGCGCCG CCCCTGCCGA TCGGCCCTCC GGAGGCACCG CTCCGGGTCC     240

CCCCCGCCAC TGCCTGGCAC CCAGGCTGCC CACCTCGCGA CCCGGGTCCT CGCTGCCGCC     300

TCGCCCGGCC CCACTGTTCT CTCCACGGGG TCTCGCCAGC TCTTTCTCGT CGCCGCCACC     360

GCCGCCCCCT TGGAGCAGCG GGTCCGCCGC GGGTCACCAT GCCCAGCAAA ACCAAGTACA     420

ACCTTGTGGA CGATGGGCAC GACTTACGGA TCCCTTTGCA CAACGAGGAC GCCTTCCAGC     480

ACGGCATCTC TTTTGAGGCC AAGTACGTGG GAAGCCTGGA TGTGCCCAGA CCCAACAGCA     540

GGGTTGAGAT CGTGGCTGCC ATGCGCAGAA TCCGGTATGA GTTTAAAGCC AAGAATATCA     600

AGAAGAAGAA AGTAAGCATC ATGGTCTCCG TGGACGGTGT CAAAGTGATT CTGAAGAAGA     660

AGAAAAAGAA AAAGGAGTGG ACGTGGGATG AGAGCAAGAT GCTGGTGATG CAGGACCCTA     720

TCTACAGGAT CTTCTATGTC TCTCATGACT CCCAAGACTT GAAAATCTTC AGCTATATCG     780

CTCGAGATGG TGCCAGCAAT ATCTTCAGAT GCAATGTCTT TAAATCCAAG AAGAAGAGCC     840

AAGCTATGAG AATCGTACGG ACAGTGGGAC AGGCCTTTGA GGTCTGCCAC AAGCTGAGCC     900

TGCAGCACAC ACAGCAGAAT GCAGATGGCC AGGAAGATGG AGAGAGCGAG AGGAACAGCG     960

ATGGCTCAGG AGACCCAGGC CGCCAGCTCA CTGGAGCTGA GAGGGTCTCC ACAGCCACCG    1020

CAGAGGAGAC CGACATTGAC GCTGTGGAGG TCCCACTCCC CGGGAATGAC ATTCTAGAAT    1080

TCAGCCGAGG TGTGACTGAC CTGGATGCTA TTGGGAAGGA CGGAGGCTCC CACATAGACA    1140

CGACGGTCTC ACCCCATCCA CAGGAGCCCA TGCTGGCAGC CTCCCCTCGC ATGCTGCTCC    1200

CTTCTTCTTC TTCCTCGAAG CCACCGGGCT TGGGCACTGG GACGCCCCTG TCCACTCACC    1260

ACCAGATGCA GCTCCTCCAG CAGCTCCTCC AGCAGCAGCA GCAGCAGACA CAAGTGGCTG    1320

TGGCTCAGGT TCACTTGCTG AAGGATCAGT TGGCTGCTGA GGCTGCGGCA CGGCTGGAGG    1380

CCCAGGCACG AGTGCACCAG CTCCTGCTAC AGAACAAAGA CATGCTTCAG CACATCTCTC    1440

TGCTGGTTAA GCAGGTGCAG GAGCTGGAAC TGAAGCTGTC AGGACAGAGC ACCATGGGCT    1500

CCCAGGACAG CTTGCTGGAG ATCACCTTCC GTTCAGGTGC CCTGCCTGTG CTCTGTGAAT    1560

CCACCACTCC TAAGCCAGAG GACCTACACT CACCACTGCT GGGCGCTGGC TTGGCTGACT    1620

TTGCCCACCC AGTGGGCAGC CCCTTAGGTA GGCGTGACTG CTTGGTGAAG CTGGAGTGCT    1680

TTCGTTTCCT CCCAGCCGAG GATAACCAGC CGATGGCACA GGGTGAGCCG CTCCTAGGTG    1740

GCCTGGAGCT CATCAAGTTC CGAGAGTCAG GCATCGCCTC AGAGTATGAG TCCAACACAG    1800

ACGAAAGCGA GGAGCGTGAC TCGTGGTCGC AGGAAGAGCT GCCACGCCTG CTCAATGTCC    1860

TACAGCGGCA GGAGTTGGGT GACAGTTTGG ATGATGAGAT CGCCGTGTAG GTGCAGGGCA    1920

AGGAGCTGGT GAAGGTGGCA GCATGATGCC AAGGGGGTCA AGTCTGCCTG TCCCCGGCTG    1980

GGGAAGCCCA GGGGAAAGCA CCGCTGAGAA AAACACCCAG GGCTGAGAGT GTAGGGTTTC    2040

AGAAGAGGGT TGGGATTTTG CTTTGGAAGG TAAAGCAGGG AAGAAAATGG ATTCCTAGAC    2100

ACAGGAATCA GCACCTGTAT TCTGCTAATG ACTGAATGGG ACGGAAGCAG GGCTTTCCAG    2160

AACCCAGGAC CTTGGGATGG GTCCGCCTTC AAGAATCACA GTTCTGGAAG GCCTGTTGCT    2220

CCCACCGTTA TAGTCAGGTT CTACTCAATC TGTCCGTGAT GTCTCAGTGG CCTACACTCT    2280

CCTGTCTCTG TGGTGCAGAT CATAAATGGA AGCCATTGAT ACCGTCTCAC GTACTTTGTT    2340
```

```
TTGGATATCA GGATGCTACA AGTTGCCTAA CCCTCCCTTA AGCTGTAGGA GAATTCCTTC    2400

CCCAGGCCCT GGCTGAGATC AGAGAGGTTG GAGGATTTCC CTCACTGCTG GGAAATTGAG    2460

ACTCTGCCAT TCAGTGAGCA TGGAGGTGAC AGCAGTCACA AGTCACAGTG AATAAACTAG    2520

GAATTTACTC TAAGTGGGGT GTTGGATGTT GCTTCTGAGG AAGCTAGGAG TATGAATAGG    2580

ATTGAGGACC CTGCAGGGAG AGCCTGGGGA GGGTTAGCCT AGGGGAGGGT TAGCCTAGAG    2640

AAGGGTTAGC CTAGGAGTGC TGATGACAGT TGTGGCAGCT CATGTAGGTG TGATTCTTCA    2700

GTTTGGAAAC CATGCCCCTT ACCCATCTCC TGCCTGCAAC CCAGCTCATA TAAACGAGGC    2760

TAAGAACTAT CATAATATCC CCTTTTCTTG CCTCAGGGGC TGTGCCTGCC TAATGAGTGC    2820

GGCCGC                                                                2826
```

(2) INFORMATION FOR SEQ ID NO:2:

(i) SEQUENCE CHARACTERISTICS:
        (A) LENGTH: 503 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Met Pro Ser Lys Thr Lys Tyr Asn Leu Val Asp Asp Gly His Asp Leu
 1               5                  10                  15

Arg Ile Pro Leu His Asn Glu Asp Ala Phe Gln His Gly Ile Ser Phe
            20                  25                  30

Glu Ala Lys Tyr Val Gly Ser Leu Asp Val Pro Arg Pro Asn Ser Arg
        35                  40                  45

Val Glu Ile Val Ala Ala Met Arg Arg Ile Arg Tyr Glu Phe Lys Ala
    50                  55                  60

Lys Asn Ile Lys Lys Lys Val Ser Ile Met Val Ser Val Asp Gly
65                  70                  75                  80

Val Lys Val Ile Leu Lys Lys Lys Lys Lys Glu Trp Thr Trp
            85                  90                  95

Asp Glu Ser Lys Met Leu Val Met Gln Asp Pro Ile Tyr Arg Ile Phe
           100                 105                 110

Tyr Val Ser His Asp Ser Gln Asp Leu Lys Ile Phe Ser Tyr Ile Ala
           115                 120                 125

Arg Asp Gly Ala Ser Asn Ile Phe Arg Cys Asn Val Phe Lys Ser Lys
       130                 135                 140

Lys Lys Ser Gln Ala Met Arg Ile Val Arg Thr Val Gly Gln Ala Phe
145                 150                 155                 160

Glu Val Cys His Lys Leu Ser Leu Gln His Thr Gln Gln Asn Ala Asp
                   165                 170                 175

Gly Gln Glu Asp Gly Glu Ser Glu Arg Asn Ser Asp Gly Ser Gly Asp
               180                 185                 190

Pro Gly Arg Gln Leu Thr Gly Ala Glu Arg Val Ser Thr Ala Thr Ala
           195                 200                 205

Glu Glu Thr Asp Ile Asp Ala Val Glu Val Pro Leu Pro Gly Asn Asp
       210                 215                 220

Ile Leu Glu Phe Ser Arg Gly Val Thr Asp Leu Asp Ala Ile Gly Lys
225                 230                 235                 240

Asp Gly Gly Ser His Ile Asp Thr Thr Val Ser Pro His Pro Gln Glu
                   245                 250                 255
```

```
Pro Met Leu Ala Ala Ser Pro Arg Met Leu Leu Pro Ser Ser Ser Ser
            260                 265                 270

Ser Lys Pro Pro Gly Leu Gly Thr Gly Thr Pro Leu Ser Thr His His
        275                 280                 285

Gln Met Gln Leu Leu Gln Gln Leu Leu Gln Gln Gln Gln Gln Gln Thr
        290                 295                 300

Gln Val Ala Val Ala Gln Val His Leu Leu Lys Asp Gln Leu Ala Ala
305                 310                 315                 320

Glu Ala Ala Ala Arg Leu Glu Ala Gln Ala Arg Val His Gln Leu Leu
                325                 330                 335

Leu Gln Asn Lys Asp Met Leu Gln His Ile Ser Leu Leu Val Lys Gln
            340                 345                 350

Val Gln Glu Leu Glu Leu Lys Leu Ser Gly Gln Ser Thr Met Gly Ser
        355                 360                 365

Gln Asp Ser Leu Leu Glu Ile Thr Phe Arg Ser Gly Ala Leu Pro Val
        370                 375                 380

Leu Cys Glu Ser Thr Thr Pro Lys Pro Glu Asp Leu His Ser Pro Leu
385                 390                 395                 400

Leu Gly Ala Gly Leu Ala Asp Phe Ala His Pro Val Gly Ser Pro Leu
                405                 410                 415

Gly Arg Arg Asp Cys Leu Val Lys Leu Glu Cys Phe Arg Phe Leu Pro
            420                 425                 430

Ala Glu Asp Asn Gln Pro Met Ala Gln Gly Glu Pro Leu Leu Gly Gly
            435                 440                 445

Leu Glu Leu Ile Lys Phe Arg Glu Ser Gly Ile Ala Ser Glu Tyr Glu
        450                 455                 460

Ser Asn Thr Asp Glu Ser Glu Glu Arg Asp Ser Trp Ser Gln Glu Glu
465                 470                 475                 480

Leu Pro Arg Leu Leu Asn Val Leu Gln Arg Gln Glu Leu Gly Asp Ser
                485                 490                 495

Leu Asp Asp Glu Ile Ala Val
            500
```

(2) INFORMATION FOR SEQ ID NO:3:

(i) SEQUENCE CHARACTERISTICS:
        (A) LENGTH: 1504 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
AAGCTTGGCA CGAGGTCAAG CAGGTGCAAG AGCTGGAACT GAAGCTGTCA GGACAGAACG    60

CCATGGGCTC CCAGGACAGC TTGCTGGAGA TCACCTTCCG CTCCGGAGCC CTGCCCGTGC   120

TCTGTGACCC CACGACCCCT AAGCCAGAGG ACCTGCATTC GCCGCCGCTG GGCGCGGGCT   180

TGGCTGACTT TGCCCACCCT GCGGGCAGCC CCTTAGGTAG GCGCGACTGC TTGGTGAAGC   240

TGGAGTGCTT TCGCTTTCTT CCGCCCGAGG ACACCCCGCC CCCAGCGCAG GGCGAGGCGC   300

TCCTGGGCGG TCTGGAGCTC ATCAAGTTCC GAGAGTCAGG CATCGCCTCG GAGTACGAGT   360

CCAACACGGA CGAGAGCGAG GAGCGCGACT CGTGGTCCCA GGAGGAGCTG CCGCGCCTGC   420

TGAATGTCCT GCAGAGGCAG GAACTGGGCG ACGGCCTGGA TGATGAGATC GCCGTGTAGG   480

TGCCGAGGGC GAGGAGATGG AGGCGGCGGC GTGGCTGGAG GGGCCGTGTC TGGCTGCTGC   540
```

```
CCGGGTAGGG GATGCCCAGT GAATGTGCAC TGCCGAGGAG AATGCCAGCC AGGGCCCGGG    600

AGAGTGTGAG GTTTCAGGAA AGTATTGAGA TTCTGCTTTG GAGGGTAAAG TGGGGAAGAA    660

ATCGGATTCC CAGAGGTGAA TCAGCTCCTC TCCTACTTGT GACTAGAGGG TGGTGGAGGT    720

AAGGCCTTCC AGAGCCCATG GCTTCAGGAG AGGGTCTCTC TCCAGGACTG CCAGGCTGCT    780

GGAGGACCTG CCCCTACCTG CTGCATCGTC AGGCTCCCAC GCTTTGTCCG TGATGCCCCC    840

CTACCCCCTC ACTCTCCCCG TCTCCATGGT CCCGACCAGG AAGGGAAGCC ATCGGTACCT    900

TCTCAGGTAC TTTGTTTCTG GATATCACGA TGCTGCGAGT TGCCTAACCC TCCCCCTACC    960

TTTATGAGAG GAATTCCTTC TCCAGGCCCT TGCTGAGATT GTAGAGATTG AGTGCTCTGG   1020

ACCGCAAAAG CCAGGCTAGT CCTTGTAGGG TGAGCATGGA ATTGGAATGT GTCACAGTGG   1080

ATAAGCTTTT AGAGGAACTG AATCCAAACA TTTTCTCCAG CCGGACATTG AATGTTGCTA   1140

CAAAGGGAGC CTTGAAGCTT TAACATGGTT CAGGCCCTTG GTGTGAGAGC CAGGGGGAG    1200

GACAGCTTGT CTGCTGCTCC AAATCACTTA GATCTGATTC CTGTTTTGAA AGTCCTGCCC   1260

TGCCTTCCTC CTGCCTGTAG CCCAGCCCAT CTAAATGGAA GCTGGGAATT GCCCCTCACC   1320

TCCCCTGTGT CCTGTCCAGC TGAAGCTTTT GCAGCACTTT ACCTCTCTGA AGCCCCAGA    1380

GGACCAGAGC CCCCAGCCTT ACCTCTCAAC CTGTCCCCTC CACTGGGCAG TGGTGGTCAG   1440

TTTTTACTGC AAAAAAAAA AAAAAGAAAA AAGAGAAAAA AAAAAAAAA ATTCCTGCGG    1500

CCGC                                                                1504

(2) INFORMATION FOR SEQ ID NO:4:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

Lys Gln Val Gln Glu Leu Glu Leu Lys Leu Ser Gly Gln Asn Ala Met
1               5                   10                  15

Gly Ser Gln Asp Ser Leu Leu Glu Ile Thr Phe Arg Ser Gly Ala Leu
            20                  25                  30

Pro Val Leu Cys Asp Pro Thr Thr Pro Lys Pro Glu Asp Leu His Ser
        35                  40                  45

Pro Pro Leu Gly Ala Gly Leu Ala Asp Phe Ala His Pro Ala Gly Ser
    50                  55                  60

Pro Leu Gly Arg Arg Asp Cys Leu Val Lys Leu Glu Cys Phe Arg Phe
65                  70                  75                  80

Leu Pro Pro Glu Asp Thr Pro Pro Ala Gln Gly Glu Ala Leu Leu
                85                  90                  95

Gly Gly Leu Glu Leu Ile Lys Phe Arg Glu Ser Gly Ile Ala Ser Glu
            100                 105                 110

Tyr Glu Ser Asn Thr Asp Glu Ser Glu Arg Asp Ser Trp Ser Gln
        115                 120                 125

Glu Glu Leu Pro Arg Leu Leu Asn Val Leu Gln Arg Gln Glu Leu Gly
    130                 135                 140

Asp Gly Leu Asp Asp Glu Ile Ala Val
145                 150
```

-continued (2) INFORMATION FOR SEQ ID NO:5:

(i) SEQUENCE CHARACTERISTICS:
        (A) LENGTH: 1430 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Met Glu Glu Asn Thr Phe Gly Val Gln Gln Ile Gln Pro Asn Val Ile
  1               5                  10                  15

Ser Val Arg Leu Phe Lys Arg Lys Val Gly Gly Leu Gly Phe Leu Val
             20                  25                  30

Lys Glu Arg Val Ser Lys Pro Pro Val Ile Ile Ser Asp Leu Ile Arg
         35                  40                  45

Gly Gly Ala Ala Glu Gln Ser Gly Leu Ile Gln Ala Gly Asp Ile Ile
     50                  55                  60

Leu Ala Val Asn Asp Arg Pro Leu Val Asp Leu Ser Tyr Asp Ser Ala
 65                  70                  75                  80

Leu Glu Val Leu Arg Gly Ile Ala Ser Glu Thr His Val Val Leu Ile
                 85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
        115                 120                 125

Pro Thr Lys Ala Val Asp Leu Ser His Gln Pro Ser Ala Ser Lys Asp
    130                 135                 140

Gln Ser Leu Ala Val Asp Arg Val Thr Gly Leu Gly Asn Gly Pro Gln
145                 150                 155                 160

His Ala Gln Gly His Gly Gln Gly Ala Gly Ser Val Ser Gln Ala Asn
                165                 170                 175

Gly Val Ala Ile Asp Pro Thr Met Lys Ser Thr Lys Ala Asn Leu Gln
            180                 185                 190

Asp Ile Gly Glu His Asp Glu Leu Leu Lys Glu Ile Glu Pro Val Leu
        195                 200                 205

Ser Ile Leu Asn Ser Gly Ser Lys Ala Thr Asn Arg Gly Gly Pro Ala
    210                 215                 220

Lys Ala Glu Met Lys Asp Thr Gly Ile Gln Val Asp Arg Asp Leu Asp
225                 230                 235                 240

Gly Lys Ser His Lys Ala Pro Pro Leu Gly Gly Asp Asn Asp Arg Val
                245                 250                 255

Phe Asn Asp Leu Trp Gly Lys Asp Asn Val Pro Val Ile Leu Asn Asn
            260                 265                 270

Pro Tyr Ser Glu Lys Glu Gln Ser Pro Thr Ser Gly Lys Gln Ser Pro
        275                 280                 285

Thr Lys Asn Gly Ser Pro Ser Arg Cys Pro Arg Phe Leu Lys Val Lys
    290                 295                 300

Asn Trp Glu Thr Asp Val Val Leu Thr Asp Thr Leu His Leu Lys Ser
305                 310                 315                 320

Thr Leu Glu Thr Gly Cys Thr Glu His Ile Cys Met Gly Ser Ile Met
                325                 330                 335

Leu Pro Ser Gln His Thr Arg Lys Pro Glu Asp Val Arg Thr Lys Asp
            340                 345                 350

Gln Leu Phe Pro Leu Ala Lys Glu Phe Leu Asp Gln Tyr Tyr Ser Ser
```

```
            355                 360                 365
Ile Lys Arg Phe Gly Ser Lys Ala His Met Asp Arg Leu Glu Glu Val
            370                 375                 380

Asn Lys Glu Ile Glu Ser Thr Ser Thr Tyr Gln Leu Lys Asp Thr Glu
385                 390                 395                 400

Leu Ile Tyr Gly Ala Lys His Ala Trp Arg Asn Ala Ser Arg Cys Val
                405                 410                 415

Gly Arg Ile Gln Trp Ser Lys Leu Gln Val Phe Asp Ala Arg Asp Cys
            420                 425                 430

Thr Thr Ala His Gly Met Phe Asn Tyr Ile Cys Asn His Val Lys Tyr
            435                 440                 445

Ala Thr Asn Lys Gly Asn Leu Arg Ser Ala Ile Thr Ile Phe Pro Gln
450                 455                 460

Arg Thr Asp Gly Lys His Asp Phe Arg Val Trp Asn Ser Gln Leu Ile
465                 470                 475                 480

Arg Tyr Ala Gly Tyr Lys Gln Pro Asp Gly Ser Thr Leu Gly Asp Pro
                485                 490                 495

Ala Asn Val Gln Phe Thr Glu Ile Cys Ile Gln Gln Gly Trp Lys Ala
            500                 505                 510

Pro Arg Gly Arg Phe Asp Val Leu Pro Leu Leu Gln Ala Asn Gly
            515                 520                 525

Asn Asp Pro Glu Leu Phe Gln Ile Pro Pro Glu Leu Val Leu Glu Val
530                 535                 540

Pro Ile Arg His Pro Lys Phe Asp Trp Phe Lys Asp Leu Gly Leu Lys
545                 550                 555                 560

Trp Tyr Gly Leu Pro Ala Val Ser Asn Met Leu Leu Glu Ile Gly Gly
                565                 570                 575

Leu Glu Phe Ser Ala Cys Pro Phe Ser Gly Trp Tyr Met Gly Thr Glu
            580                 585                 590

Ile Gly Val Arg Asp Tyr Cys Asp Asn Ser Arg Tyr Asn Ile Leu Glu
            595                 600                 605

Glu Val Ala Lys Lys Met Asp Leu Asp Met Arg Lys Thr Ser Ser Leu
610                 615                 620

Trp Lys Asp Gln Ala Leu Val Glu Ile Asn Ile Ala Val Leu Tyr Ser
625                 630                 635                 640

Phe Gln Ser Asp Lys Val Thr Ile Val Asp His His Ser Ala Thr Glu
                645                 650                 655

Ser Phe Ile Lys His Met Glu Asn Glu Tyr Arg Cys Arg Gly Gly Cys
            660                 665                 670

Pro Ala Asp Trp Val Trp Ile Val Pro Pro Met Ser Gly Ser Ile Thr
            675                 680                 685

Pro Val Phe His Gln Glu Met Leu Asn Tyr Arg Leu Thr Pro Ser Phe
690                 695                 700

Glu Tyr Gln Pro Asp Pro Trp Asn Thr His Val Trp Lys Gly Thr Asn
705                 710                 715                 720

Gly Thr Pro Thr Lys Arg Arg Ala Ile Gly Phe Lys Lys Leu Ala Glu
                725                 730                 735

Ala Val Lys Phe Ser Ala Lys Leu Met Gly Gln Ala Met Ala Lys Arg
            740                 745                 750

Val Lys Ala Thr Ile Leu Tyr Ala Thr Glu Thr Gly Lys Ser Gln Ala
            755                 760                 765

Tyr Ala Lys Thr Leu Cys Glu Ile Phe Lys His Ala Phe Asp Ala Lys
770                 775                 780
```

-continued

```
Ala Met Ser Met Glu Glu Tyr Asp Ile Val His Leu Glu His Glu Ala
785                 790                 795                 800

Leu Val Leu Val Val Thr Ser Thr Phe Gly Asn Gly Asp Pro Pro Glu
            805                 810                 815

Asn Gly Glu Lys Phe Gly Cys Ala Leu Met Glu Met Arg His Pro Asn
        820                 825                 830

Ser Val Gln Glu Arg Lys Ser Tyr Lys Val Arg Phe Asn Ser Val
    835                 840                 845

Ser Ser Tyr Ser Asp Ser Arg Lys Ser Ser Gly Asp Gly Pro Asp Leu
850                 855                 860

Arg Asp Asn Phe Glu Ser Thr Gly Pro Leu Ala Asn Val Arg Phe Ser
865                 870                 875                 880

Val Phe Gly Leu Gly Ser Arg Ala Tyr Pro His Phe Cys Ala Phe Gly
                885                 890                 895

His Ala Val Asp Thr Leu Leu Glu Leu Gly Gly Glu Arg Ile Leu
                900                 905                 910

Lys Met Arg Glu Gly Asp Glu Leu Cys Gly Gln Glu Glu Ala Phe Arg
            915                 920                 925

Thr Trp Ala Lys Lys Val Phe Lys Ala Ala Cys Asp Val Phe Cys Val
        930                 935                 940

Gly Asp Asp Val Asn Ile Glu Lys Pro Asn Asn Ser Leu Ile Ser Asn
945                 950                 955                 960

Asp Arg Ser Trp Lys Arg Asn Lys Phe Arg Leu Thr Tyr Val Ala Glu
                965                 970                 975

Ala Pro Asp Leu Thr Gln Gly Leu Ser Asn Val His Lys Lys Arg Val
            980                 985                 990

Ser Ala Ala Arg Leu Leu Ser Arg Gln Asn Leu Gln Ser Pro Lys Phe
        995                 1000                1005

Ser Arg Ser Thr Ile Phe Val Arg Leu His Thr Asn Gly Asn Gln Glu
    1010                1015                1020

Leu Gln Tyr Gln Pro Gly Asp His Leu Gly Val Phe Pro Gly Asn His
025                 1030                1035                1040

Glu Asp Leu Val Asn Ala Leu Ile Glu Arg Leu Glu Asp Ala Pro Pro
                1045                1050                1055

Ala Asn His Val Val Lys Val Glu Met Leu Glu Glu Arg Asn Thr Ala
            1060                1065                1070

Leu Gly Val Ile Ser Asn Trp Lys Asp Glu Ser Arg Leu Pro Pro Cys
        1075                1080                1085

Thr Ile Phe Gln Ala Phe Lys Tyr Tyr Leu Asp Ile Thr Thr Pro Pro
    1090                1095                1100

Thr Pro Leu Gln Leu Gln Gln Phe Ala Ser Leu Ala Thr Asn Glu Lys
105                 1110                1115                1120

Glu Lys Gln Arg Leu Leu Val Leu Ser Lys Gly Leu Gln Glu Tyr Glu
                1125                1130                1135

Glu Trp Lys Trp Gly Lys Asn Pro Thr Met Val Glu Val Leu Glu Glu
            1140                1145                1150

Phe Pro Ser Ile Gln Met Pro Ala Thr Leu Leu Leu Thr Gln Leu Ser
        1155                1160                1165

Leu Leu Gln Pro Arg Tyr Tyr Ser Ile Ser Ser Ser Pro Asp Met Tyr
    1170                1175                1180

Pro Asp Glu Val His Leu Thr Val Ala Ile Val Ser Tyr His Thr Arg
185                 1190                1195                1200
```

-continued

Asp Gly Glu Gly Pro Val His His Gly Val Cys Ser Ser Trp Leu Asn
            1205                1210                1215

Arg Ile Gln Ala Asp Asp Val Val Pro Cys Phe Val Arg Gly Ala Pro
        1220                1225                1230

Ser Phe His Leu Pro Arg Asn Pro Gln Val Pro Cys Ile Leu Val Gly
            1235                1240                1245

Pro Gly Thr Gly Ile Ala Pro Phe Arg Ser Phe Trp Gln Gln Arg Gln
        1250                1255                1260

Phe Asp Ile Gln His Lys Gly Met Asn Pro Cys Pro Met Val Leu Val
265                 1270                1275                1280

Phe Gly Cys Arg Gln Ser Lys Ile Asp His Ile Tyr Arg Glu Glu Thr
            1285                1290                1295

Leu Gln Ala Lys Asn Lys Gly Val Phe Arg Glu Leu Tyr Thr Ala Tyr
            1300                1305                1310

Ser Arg Glu Pro Asp Arg Pro Lys Lys Tyr Val Gln Asp Val Leu Gln
            1315                1320                1325

Glu Gln Leu Ala Glu Ser Val Tyr Arg Ala Leu Lys Glu Gln Gly Gly
        1330                1335                1340

His Ile Tyr Val Cys Gly Asp Val Thr Met Ala Ala Asp Val Leu Lys
345                 1350                1355                1360

Ala Ile Gln Arg Ile Met Thr Gln Gln Gly Lys Leu Ser Glu Glu Asp
            1365                1370                1375

Ala Gly Val Phe Ile Ser Arg Leu Arg Asp Asp Asn Arg Tyr His Glu
            1380                1385                1390

Asp Ile Phe Gly Val Thr Leu Arg Thr Tyr Glu Val Thr Asn Arg Leu
        1395                1400                1405

Arg Ser Glu Ser Ile Ala Phe Ile Glu Glu Ser Lys Lys Asp Ala Asp
    1410                1415                1420

Glu Val Phe Ser Ser Pro
425                 1430

(2) INFORMATION FOR SEQ ID NO:6:

(i) SEQUENCE CHARACTERISTICS:
        (A) LENGTH: 1554 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

Met Glu Asp His Met Phe Gly Val Gln Gln Ile Gln Pro Asn Val Ile
1               5                   10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
        35                  40                  45

Gly Gly Ala Ala Glu Gln Ser Gly Leu Ile Gln Ala Gly Asp Ile Ile
    50                  55                  60

Leu Ala Val Asn Gly Arg Pro Leu Val Asp Leu Ser Tyr Asp Ser Ala
65                  70                  75                  80

Leu Glu Val Leu Arg Gly Ile Ala Ser Glu Thr His Val Val Leu Ile
                85                  90                  95

Leu Arg Gly Pro Glu Gly Phe Thr Thr His Leu Glu Thr Thr Phe Thr
            100                 105                 110

-continued

```
Gly Asp Gly Thr Pro Lys Thr Ile Arg Val Thr Gln Pro Leu Gly Pro
            115                 120                 125

Pro Thr Lys Ala Val Asp Leu Ser His Gln Pro Pro Ala Gly Lys Glu
    130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
                165                 170                 175

Gly Leu Ala Pro Arg Pro Pro Gly Gln Asp Pro Ala Lys Lys Ala Thr
            180                 185                 190

Arg Val Ser Leu Gln Gly Arg Gly Glu Asn Asn Glu Leu Leu Lys Glu
            195                 200                 205

Ile Glu Pro Val Leu Ser Leu Leu Thr Ser Gly Ser Arg Gly Val Lys
            210                 215                 220

Gly Gly Ala Pro Ala Lys Ala Glu Met Lys Asp Met Gly Ile Gln Val
225                 230                 235                 240

Asp Arg Asp Leu Asp Gly Lys Ser His Lys Pro Leu Pro Leu Gly Val
                245                 250                 255

Glu Asn Asp Arg Val Phe Asn Asp Leu Trp Gly Lys Gly Asn Val Pro
                260                 265                 270

Val Val Leu Asn Asn Pro Tyr Ser Glu Lys Gln Pro Pro Thr Ser
            275                 280                 285

Gly Lys Gln Ser Pro Thr Lys Asn Gly Ser Pro Ser Lys Cys Pro Arg
            290                 295                 300

Phe Leu Lys Val Lys Asn Trp Glu Thr Glu Val Val Leu Thr Asp Thr
305                 310                 315                 320

Leu His Leu Lys Ser Thr Leu Glu Thr Gly Cys Thr Glu Tyr Ile Cys
                325                 330                 335

Met Gly Ser Ile Met His Pro Ser Gln His Ala Arg Arg Pro Glu Asp
            340                 345                 350

Val Arg Thr Lys Gly Gln Leu Phe Pro Leu Ala Lys Glu Phe Ile Asp
            355                 360                 365

Gln Tyr Tyr Ser Ser Ile Lys Arg Phe Gly Ser Lys Ala His Met Glu
    370                 375                 380

Arg Leu Glu Glu Val Asn Lys Glu Ile Asp Thr Thr Ser Thr Tyr Gln
385                 390                 395                 400

Leu Lys Asp Thr Glu Leu Ile Tyr Gly Ala Lys His Ala Trp Arg Asn
                405                 410                 415

Ala Ser Arg Cys Val Gly Arg Ile Gln Trp Ser Lys Leu Gln Val Phe
            420                 425                 430

Asp Ala Arg Asp Cys Thr Thr Ala His Gly Met Phe Asn Tyr Ile Cys
            435                 440                 445

Asn His Val Lys Tyr Ala Thr Asn Lys Gly Asn Leu Arg Ser Ala Ile
    450                 455                 460

Thr Ile Phe Pro Gln Arg Thr Asp Gly Lys His Asp Phe Arg Val Trp
465                 470                 475                 480

Asn Ser Gln Leu Ile Arg Tyr Ala Gly Tyr Lys Gln Pro Asp Gly Ser
                485                 490                 495

Thr Leu Gly Asp Pro Ala Asn Val Gln Phe Thr Glu Ile Cys Ile Gln
            500                 505                 510

Gln Gly Trp Lys Pro Pro Arg Gly Arg Phe Asp Val Leu Pro Leu Leu
            515                 520                 525

Leu Gln Ala Asn Gly Asn Asp Pro Glu Leu Phe Gln Ile Pro Pro Glu
```

-continued

```
        530                 535                 540
Leu Val Leu Glu Val Pro Ile Arg His Pro Lys Phe Glu Trp Phe Lys
545                 550                 555                 560

Asp Leu Gly Leu Lys Trp Tyr Gly Leu Pro Ala Val Ser Asn Met Leu
                565                 570                 575

Leu Glu Ile Gly Gly Leu Glu Phe Ser Ala Cys Pro Phe Ser Gly Trp
                580                 585                 590

Tyr Met Gly Thr Glu Ile Gly Val Arg Asp Tyr Cys Asp Asn Ser Arg
                595                 600                 605

Tyr Asn Ile Leu Glu Glu Val Ala Lys Lys Met Asn Leu Asp Met Arg
                610                 615                 620

Lys Thr Ser Ser Leu Trp Lys Asp Gln Ala Leu Val Glu Ile Asn Ile
625                 630                 635                 640

Ala Val Leu Tyr Ser Phe Gln Ser Asp Lys Val Thr Ile Val Asp His
                645                 650                 655

His Ser Ala Thr Glu Ser Phe Ile Lys His Met Glu Asn Glu Tyr Arg
                660                 665                 670

Cys Arg Gly Gly Cys Pro Ala Asp Trp Val Trp Ile Val Pro Pro Met
                675                 680                 685

Ser Gly Ser Ile Thr Pro Val Phe His Gln Glu Met Leu Asn Tyr Arg
                690                 695                 700

Leu Thr Pro Ser Phe Glu Tyr Gln Pro Asp Pro Trp Asn Thr His Val
705                 710                 715                 720

Trp Lys Gly Thr Asn Gly Thr Pro Thr Lys Arg Arg Ala Ile Gly Phe
                725                 730                 735

Lys Lys Leu Ala Glu Ala Val Lys Phe Ser Ala Lys Leu Met Gly Gln
                740                 745                 750

Ala Met Ala Lys Arg Val Lys Ala Thr Ile Leu Tyr Ala Thr Glu Thr
                755                 760                 765

Gly Lys Ser Gln Ala Tyr Ala Lys Thr Leu Cys Glu Ile Phe Lys His
                770                 775                 780

Ala Phe Asp Ala Lys Val Met Ser Met Glu Glu Tyr Asp Ile Val His
785                 790                 795                 800

Leu Glu His Glu Thr Leu Val Leu Val Val Thr Ser Thr Phe Gly Asn
                805                 810                 815

Gly Asp Pro Pro Glu Asn Gly Glu Lys Phe Gly Cys Ala Leu Met Glu
                820                 825                 830

Met Arg His Pro Asn Ser Val Gln Glu Glu Arg Lys Ser Tyr Lys Val
                835                 840                 845

Arg Phe Asn Ser Val Ser Ser Tyr Ser Asp Ser Gln Lys Ser Ser Gly
                850                 855                 860

Asp Gly Pro Asp Leu Arg Asp Asn Phe Glu Ser Ala Gly Pro Leu Ala
865                 870                 875                 880

Asn Val Arg Phe Ser Val Phe Gly Leu Gly Ser Arg Ala Tyr Pro His
                885                 890                 895

Phe Cys Ala Phe Gly His Ala Val Asp Thr Leu Leu Glu Glu Leu Gly
                900                 905                 910

Gly Glu Arg Ile Leu Lys Met Arg Glu Gly Asp Glu Leu Cys Gly Gln
                915                 920                 925

Glu Glu Ala Phe Arg Thr Trp Ala Lys Lys Val Phe Lys Ala Ala Cys
                930                 935                 940

Asp Val Phe Cys Val Gly Asp Asp Val Asn Ile Glu Lys Ala Asn Asn
945                 950                 955                 960
```

-continued

Ser Leu Ile Ser Asn Asp Arg Ser Trp Lys Arg Asn Lys Phe Arg Leu
              965                 970                 975

Thr Phe Val Ala Glu Ala Pro Glu Leu Thr Gln Gly Leu Ser Asn Val
              980                 985                 990

His Lys Lys Arg Val Ser Ala Ala Arg Leu Leu Ser Arg Gln Asn Leu
              995                1000                1005

Gln Ser Pro Lys Ser Ser Arg Ser Thr Ile Phe Val Arg Leu His Thr
    1010                1015                1020

Asn Gly Ser Gln Glu Leu Gln Tyr Gln Pro Gly Asp His Leu Gly Val
025                 1030                1035                1040

Phe Pro Gly Asn His Glu Asp Leu Val Asn Ala Leu Ile Glu Arg Leu
              1045                1050                1055

Glu Asp Ala Pro Pro Val Asn Gln Met Val Lys Val Glu Leu Leu Glu
              1060                1065                1070

Glu Arg Asn Thr Ala Leu Gly Val Ile Ser Asn Trp Thr Asp Glu Leu
              1075                1080                1085

Arg Leu Pro Pro Cys Thr Ile Phe Gln Ala Phe Lys Tyr Tyr Leu Asp
              1090                1095                1100

Ile Thr Thr Pro Pro Thr Pro Leu Gln Leu Gln Gln Phe Ala Ser Leu
105                 1110                1115                1120

Ala Thr Ser Glu Lys Glu Lys Gln Arg Leu Leu Val Leu Ser Lys Gly
              1125                1130                1135

Leu Gln Glu Tyr Glu Glu Trp Lys Trp Gly Lys Asn Pro Thr Ile Val
              1140                1145                1150

Glu Val Leu Glu Glu Phe Pro Ser Ile Gln Met Pro Ala Thr Leu Leu
              1155                1160                1165

Leu Thr Gln Leu Ser Leu Leu Gln Pro Arg Tyr Tyr Ser Ile Ser Ser
              1170                1175                1180

Ser Pro Asp Met Tyr Pro Asp Glu Val His Leu Thr Val Ala Ile Val
185                 1190                1195                1200

Ser Tyr Arg Thr Arg Asp Gly Glu Gly Pro Ile His His Gly Val Cys
              1205                1210                1215

Ser Ser Trp Leu Asn Arg Ile Gln Ala Asp Glu Leu Val Pro Cys Phe
              1220                1225                1230

Val Arg Gly Ala Pro Ser Phe His Leu Pro Arg Asn Pro Gln Val Pro
              1235                1240                1245

Cys Ile Leu Val Gly Pro Gly Thr Gly Ile Ala Pro Phe Arg Ser Phe
              1250                1255                1260

Trp Gln Gln Arg Gln Phe Asp Ile Gln His Lys Gly Met Asn Pro Cys
265                 1270                1275                1280

Pro Met Val Leu Val Phe Gly Cys Arg Gln Ser Lys Ile Asp His Ile
              1285                1290                1295

Tyr Arg Glu Glu Thr Leu Gln Ala Lys Asn Lys Gly Val Phe Arg Glu
              1300                1305                1310

Leu Tyr Thr Ala Tyr Ser Arg Glu Pro Asp Lys Pro Lys Lys Tyr Val
              1315                1320                1325

Gln Asp Ile Leu Gln Glu Gln Leu Ala Glu Ser Val Tyr Arg Ala Leu
    1330                1335                1340

Lys Glu Gln Gly Gly His Ile Tyr Val Cys Gly Asp Val Thr Met Ala
345                 1350                1355                1360

Ala Asp Val Leu Lys Ala Ile Gln Arg Ile Met Thr Gln Gln Gly Lys
              1365                1370                1375

```
Leu Ser Ala Glu Asp Ala Gly Val Phe Ile Ser Arg Met Arg Asp Asp
            1380                1385                1390

Asn Arg Tyr His Glu Asp Ile Phe Gly Val Thr Leu Arg Thr Tyr Glu
        1395                1400                1405

Val Thr Asn Arg Leu Arg Ser Glu Ser Ile Ala Phe Ile Glu Glu Ser
1410                1415                1420

Lys Lys Asp Thr Asp Glu Gly Phe Gln Leu Leu Thr Gly Pro Ser Cys
425                 1430                1435                1440

Pro Ala Gly Cys Lys Phe Cys Lys Arg Gly Gln Thr Leu Leu Asn Leu
                1445                1450                1455

Ser Ser Gly Thr Pro Cys Gly Pro Arg Ser Ala Ser Cys Pro Cys Arg
            1460                1465                1470

Cys Ala Leu Val Ser Leu Leu Gly Leu Leu Ala Pro Gln Trp Phe Pro
        1475                1480                1485

Arg Pro Ser Trp Val Tyr Ser Leu Ser Phe Pro Ala Ala Met Gln Cys
    1490                1495                1500

Phe Ser Asn Leu Gln Trp Leu Leu Gln Asn Ser Val Pro Thr Pro Ser
505                 1510                1515                1520

Leu Ala Asp Lys Gly Asn Ser Arg Val His Glu Thr Thr Gly Thr Trp
                1525                1530                1535

Pro Ser Leu Trp Gly Phe Phe Ser Leu Gly Phe Pro Trp Lys Gly Cys
            1540                1545                1550

Arg Asn
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:7:

GACTAGTCGA CTGAAGAGAA CACGTTTGGG                                    30

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TCTGCAGATC TCAGTGGGCC TTGGAGCCAA A                                  31

CAPON: A PROTEIN ASSOCIATED WITH NEURONAL NITRIC OXIDE SYNTHASE

The U.S. Government has a paid-up license in this invention and the right in limited circumstances to require the patent owner to license others on reasonable terms as provided for by the terms of Research Scientist Award MH-18501 awarded by the National Institutes of Health and USPHS DA0074.

TECHNICAL AREA OF THE INVENTION

The invention relates to the area of neurotransmitter regulation. More particularly, the invention relates to the regulation of neuronal nitric oxide synthase.

BACKGROUND OF THE INVENTION

Studies of neuronally-derived nitric oxide (NO) have revealed many roles for this gaseous messenger molecule (Moncada, 1994; Yun et al., 1996). In the peripheral nervous system, NO mediates nonadrenergic, noncholinergic neurotransmission, serving as an effector of autonomic neurons on smooth muscle. NO has been implicated in several forms of neuronal plasticity, such as LTP (for a review see Huang, 1997). Studies in mice with a targeted genomic deletion of the NO biosynthetic enzyme, neuronal NO synthase (nNOS), have shown that NO mediates a substantial portion of the neurotoxicity associated with stroke (Huang et al., 1994). In the brain, NO and citrulline are produced from arginine predominantly by a neuronal isoform of NOS (nNOS) (Huang et al., 1993), although endothelial NOS (eNOS) may also occur in neurons (Dinerman et al., 1994; O'Dell et al., 1994). Most neurotransmitters are stored in synaptic vesicles and neurotransmitter effects are elicited following the exocytosis of transmitter into the synaptic space. For an evanescent transmitter such as NO there is no storage pool and newly synthesized NO is used as it is made. NO synthesis is triggered by the influx of calcium, which, when complexed with calmodulin, activates the biosynthetic activity of NOS (Bredt and Snyder, 1990).

Because NO lacks vesicular storage and depends on new synthesis for its release, nNOS must be associated with the plasma membrane. Subcellular fractionation indicates that roughly half of brain nNOS is soluble and half particulate (Bredt, 1996; Hecker et al., 1994). Recently, Bredt and associates showed that nNOS is targeted to membranes by binding to syntrophin, PSD95/SAP90, or PSD93 (Brenman et al., 1996; Brenman et al., 1996). These proteins are enriched in synaptic densities and interact with nNOS through PDZ domains, consensus sequences of about 100 amino acids that are found in proteins which tend to be associated with cell-cell junctions (Ponting and Phillips, 1995). The nNOS/PSD95 interaction involves a portion of nNOS which includes its sole PDZ domain and the second PDZ domain of PSD95. PSD95 was first isolated from postsynaptic densities (Cho et al., 1992) but also occurs in presynaptic nerve terminals (Kistner et al., 1993) and clusters neurotransmitter receptors and ion channels at synaptic sites (Kornau et al., 1997). For instance, the NMDA receptor and several potassium channels are associated with PSD95 at synapses (Kornau et al., 1995). The linking of NMDA receptors to nNOS by PSD95 may explain why calcium influx following NMDA receptor activation leads to a tightly coupled nNOS activation (Brenman et al., 1996). Indeed, the effects of NO appear to be intimately tied to the NMDA receptor. For example, NMDA receptor-mediated neurotoxicity (Dawson and Dawson, 1996), neurotransmitter release (Schuman and Madison, 1994), and cGMP elevations (Bredt and Snyder, 1989; Garthwaite et al., 1989) each require nNOS and are blocked by nNOS-specific inhibitors. Moreover, NO can directly modulate NMDA receptors (Lipton and Stamler, 1994).

There is a continuing need in the art of neurotransmitter regulation for methods of affecting the activity of neuronal NOS, so that one can manipulate NO levels when required for therapeutic effect in such disorders.

SUMMARY OF THE INVENTION

It is an object of the invention to provide an isolated mammalian Capon (Carboxy-terminal PDZ ligand of nNOS) protein.

It is another object of the invention to provide a fusion protein comprising at least eight contiguous amino acids selected from the Capon amino acid sequence shown in SEQ ID NO:2.

It is yet another object of the invention to provide an isolated polypeptide consisting of at least eight contiguous amino acids of Capon as shown in SEQ ID NO:2 and capable of binding an nNOS PDZ domain.

It is still another object of the invention to provide a preparation of antibodies which specifically bind to a Capon protein as shown in SEQ ID NO:2 or 4.

It is even another object of the invention to provide a subgenomic polynucleotide which encodes a Capon protein as shown in SEQ ID NO:2 or 4.

It is yet another object of the invention to provide a recombinant DNA construct for expressing Capon antisense nucleic acids.

It is still another object of the invention to provide a method of inhibiting a mammalian neuronal nitric oxide synthase (nNOS).

It is even another object of the invention to provide methods of screening test compounds for the ability to decrease or augment the activity of nNOS.

These and other objects of the invention are provided by one or more of the embodiments described below. One embodiment of the invention provides an isolated mammalian Capon protein which has the sequence shown in SEQ ID NO:2 or 4, and naturally occurring biologically active variants thereof.

Another embodiment of the invention provides a mammalian Capon fusion protein which comprises two protein segments fused to each other by means of a peptide bond, wherein one of the protein segments consists of at least eight contiguous amino acids selected from the amino acid sequence shown in SEQ ID NO:2 or 4.

Yet another embodiment of the invention provides an isolated polypeptide which consists of at least eight contiguous amino acids of Capon as shown in SEQ ID NO:2 or 4, wherein the polypeptide binds to an nNOS PDZ domain.

Still another embodiment of the invention provides a preparation of antibodies which specifically bind to a mammalian Capon protein as shown in SEQ ID NO:2 or 4.

Even another embodiment of the invention provides a subgenomic polynucleotide which encodes a Capon protein as shown in SEQ ID NO:2 or 4.

Yet another embodiment of the invention provides a recombinant DNA construct for expressing Capon antisense nucleic acids, comprising a promoter and a coding sequence for Capon consisting of at least 12 contiguous base pairs selected from SEQ ID NO:1 or 3, wherein the coding sequence is in an inverted orientation with respect to the promoter, such that upon transcription from the promoter an RNA is produced that is complementary to native mRNA encoding Capon.

Still another embodiment of the invention provides a method of decreasing a mammalian nNOS activity, comprising the step of contacting a nNOS with a Capon protein having an amino acid sequence as shown in SEQ ID NO:2 or 4.

Even another embodiment of the invention provides a method of screening test compounds for the ability to decrease or augment nNOS activity. The method comprises the steps of: (a) contacting a test compound with a mixture of a mammalian Capon protein and a polypeptide comprising an nNOS PDZ domain; and (b) measuring the amount of Capon or the polypeptide that is bound or unbound in the presence of the test compound, a test compound that decreases the amount of bound Capon or the polypeptide being a potential drug for increasing nNOS activity, and a test compound that increases the amount of the polypeptide or Capon that are bound being a potential drug for decreasing nNOS activity.

Yet another embodiment of the invention provides a method of screening test compounds for the ability to decrease or augment nNOS activity comprising the steps of: (a) contacting a cell with a test compound, wherein the cell comprises: i) a first fusion protein comprising (1) a DNA binding domain or a transcriptional activation domain, and (2) all or a portion of a mammalian Capon protein, wherein the portion consists of a contiguous sequence of amino acids selected from the amino acid sequence shown in SEQ ID NO:2 or 4, wherein the portion is capable of binding to nNOS; ii) a second fusion protein comprising (1) a transcriptional activation domain or a DNA binding domain and (2) all or a portion of nNOS, wherein the portion comprises a PDZ domain, or a naturally occurring biologically active variant thereof, wherein the interaction of the portion of the Capon protein with the portion of nNOS reconstitutes a sequence-specific transcriptional activating factor, wherein when the first fusion protein comprises a DNA binding domain the second fusion protein comprises a transcriptional activation domain and when the first fusion protein comprises a transcriptional activation domain the second fusion protein comprises a DNA binding domain; and iii) a reporter gene comprising a DNA sequence to which the DNA binding domain of the first fusion protein specifically binds; and (b) measuring the expression of the reporter gene, a test compound that increases the expression of the reporter gene being a potential drug for decreasing nNOS activity, and a test compound that decreases the expression of the reporter gene being a potential drug for augmenting nNOS activity.

Even another embodiment of the invention provides a method of screening test compounds for the ability to decrease or augment nNOS activity comprising the steps of: (a) contacting a cell with a test compound, wherein the cell comprises: (i) a first expression vector comprising a subgenomic polynucleotide encoding at least the PDZ domain of nNOS or a naturally occurring biologically active variant thereof; (ii) a second expression vector comprising a subgenomic polynucleotide encoding at least the portion of Capon or a naturally occurring biologically active variant thereof, wherein the portion of Capon is capable of binding to nNOS; and (b) measuring the amount of cGMP, NO, or citrulline in the cell, a test compound that increases the amount of cGMP, NO, or citrulline being a potential drug for augmenting nNOS activity, and a test compound that decreases the amount of cGMP being a potential drug for decreasing nNOS activity.

According to still another embodiment a method is provided for diagnosing a neurological disease or a propensity for a neurological disease, comprising: determining number of glutamine repeats present in a Capon protein of a patient wherein a number greater than 6 indicates a neurologic disease or a propensity therefor.

According to still another embodiment a method is provided for diagnosing a nuerological disease or a propensity for a neurological disease, comprising: determining number of CAG repeats in a Capon gene of a patient, wherein a number greater than 6 indicates a neurologic disease or a propensity therefor.

Another aspect of the invention is a cell comprising one or more recombinant nucleic acid molecules. The cell comprises: (i) a first expression vector comprising a subgenomic polynucleotide encoding at least the PDZ domain of nNOS or a naturally occurring biologically active variant thereof; and (ii) a second expression vector comprising a subgenomic polynucleotide encoding at least a portion of Capon or a naturally occurring biologically active variant thereof, wherein the portion of Capon is capable of binding to nNOS.

Another aspect of the invention is a cell comprising one or more recombinant nucleic acid molecules. The cell comprises: i) a nucleotide construct encoding a first fusion protein comprising (1) a DNA binding domain or a transcriptional activation domain, and (2) all or a portion of a mammalian Capon protein, wherein the portion consists of a contiguous sequence of amino acids selected from the amino acid sequence shown in SEQ ID NO:2 or 4, wherein the portion is capable of binding to nNOS; ii) a nucleotide construct encoding a second fusion protein comprising (1) a transcriptional activation domain or a DNA binding domain and (2) all or a portion of nNOS, wherein the portion comprises a PDZ domain, or a naturally occurring biologically active variant thereof, wherein the interaction of the portion of the Capon protein with the portion of nNOS reconstitutes a sequence-specific transcriptional activating factor, wherein when the first fusion protein comprises a DNA binding domain the second fusion protein comprises a transcriptional activation domain, and when the first fusion protein comprises a transcriptional activation domain the second fusion protein comprises a DNA binding domain; and iii) a reporter gene comprising a DNA sequence to which the DNA binding domain of the first fusion protein specifically binds, wherein upon reconstitution of the sequence specific transactivating factor, expression of the reporter gene is increased.

The present invention thus provides the art with the information that Capon, a heretofore unknown protein, regulates the activity of neuronal nitric oxide synthase. Capon can be used, inter alia, in assays to screen for substances which have the ability to decrease or augment neuronal nitric oxide synthase activity.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 1A–1C. Cloning of the CAPON cDNA and distribution of CAPON mRNA. (FIG. 1A) CAPON specifically interacts with nNOS in the yeast two-hybrid system. Yeast were transformed with the indicated Gal4 activation domain (AD) and Gal4 DNA-binding domain (BD) plasmids and grown on plates containing histidine. A typical filter lift is shown in which b-galactosidase activity was detected by the appearance of a blue precipitate. pAD-CAPON1, comprising the last 125 amino acids of CAPON, activates lacZ transcription in the presence of pBD-nNOS (2-377) but not with plasmids the first three PDZ domains of PSD95 (amino acids 20–364) or the second PDZ domain of PSD93 (amino acids 116–421).

(FIG. 1B) Amino acid sequence of rat CAPON and alignment with a partial human sequence. The underlined sequence corresponds to the putative PTB domain. The bracketed sequence is encoded by a CAG repeat. A human expressed sequence tag (EST) (accession number R19867 SEQ ID NO:3) obtained from a library derived from infant brain contains a 459 bp open reading frame with homology to the C-terminus of the CAPON cDNA ($p=5.1 \times 10^{-17}$). The conceptual translation of this clone reveals a protein with 92% amino acid identity with the rat protein.

(FIG. 1C) CAPON is enriched in neuronal structures. Northern (RNA) blot analysis reveals that several CAPON transcripts are present, and these transcripts are enriched in neuronal tissues.

FIGS. 2A–2E. Interaction of CAPON and nNOS.

(FIG. 2A) CAPON binds to nNOS, but not eNOS or iNOS. Bacterially expressed GST, GST-PIN, and GST-CAPON were bound to glutathione agarose and then incubated with lysates of HEK293 cells transfected with expression plasmids for the indicated isoforms of NOS. After extensive washing of the resins, bound NOS was detected with isoform specific antibodies. While nNOS binds to both GST-PIN and GST-CAPON, neither eNOS or iNOS bind to either protein. Input=10% of starting material applied to each resin.

(FIG. 2B) A GST-NOS fusion protein specifically binds to rat brain CAPON. A fusion protein consisting of GST and amino acids 1–100 of nNOS was bound to glutathione agarose and then incubated with cerebellar supernatants. After extensive washing, CAPON is detected on the NOS resin but not on the control GST resin. A second ~48 kD band is also detected with this antibody, but fails to interact with nNOS. This band may represent a cross-reactive protein, an alternatively spliced isoform of CAPON, or a degradation product.

(FIG. 2C) CAPON interacts with nNOS directly. HEK293 lysates transfected with a expression plasmid containing the nNOS cDNA or empty vector were resolved by electrophoresis, transferred to nitrocellulose, and probed with radiolabeled CAPON (see Methods). Purified nNOS is recognized with this probe, along with a comigrating band detected in NOS-transfected but not mock-transfected cells.

(FIG. 2D) CAPON and nNOS complexes are detectable in cerebellar lysates (I). Cerebellar supernatants were prepared from wild-type (+/+) and nNOS knockout (−/−) mice and incubated with the 2', 5', ADP-sepharose, an nNOS-affinity resin. Only CAPON derived from supernatants of wild-type and not knockout animals was capable of binding the resin indicating that the presence of nNOS is required for CAPON to bind to the resin. CAPON levels were decreased in knockout animals, presumably due to decreased stability in the absence of the nNOS binding partner. A lower molecular weight band (arrowhead), frequently detected with the anti-CAPON antibody, bound weakly to the resin in an nNOS-specific manner as well. Input=20% of lysate used for binding.

(FIG. 2E) CAPON and nNOS complexes are detectable in cerebellar lysates (II). An antibody to CAPON (5 mg) specifically coprecipitates nNOS, while comprable amounts of antibody to the G-protein subunit bl, cyclin-dependent kinase 2, and preimmune serum fail to coprecipitate nNOS. Enrichment of nNOS in CAPON immunoprecipitates was specific as a control protein, protein kinase C- b I/II did not display similar enrichment. Input=10% of lysate used for immunoprecipitation.

(FIG. 3A) Comparison of nNOS-IR (immunoreactivity), CAPON-IR, and CAPON in situ hybridization patterns in sagittal sections of adult rat. Islands of Calleja (solid arrowhead); supraoptic nucleus (open arrowhead); AOB, accessory olfactory bulb; C, colliculi; Cb, cerebellum; Cx, cerebral cortex; OB, olfactory bulb. Immunohistochemical nonspecific labelling ("Block") was determined using a CAPON antibody pre-absorbed with the antigenic peptide. Nonspecific hybridization ("Sense") was detected using a sense probe.

(FIG. 3B) Comparison of cellular localization of nNOS-IR and CAPON-IR in adult rat brain. CAPON-IR (a) and nNOS-IR (b) hypothalamic neurons, solid arrowheads indicate IR dendritic processes. CAPON-IR (c) and nNOS-IR (d) of the supraoptic nucleus. CAPON-IR (e) and nNOS-IR (f) cell bodies of the nucleus of the trapezoid body separated by unreactive fascicles of nerve fibers. Adjacent is the pontine nucleus (Pn) which exhibits both CAPON and nNOS-IR (e,f). CAPON-IR (g) and nNOS-IR (h) in the cerebellum. Molecular cell layer (Mol); granular cell layer (Gr). Micrographs e,f, (100×); c, d, g, h, (200×); a, b (400×).

FIGS. 4A–4C. The PDZ domain of nNOS interacts with the C-terminus of CAPON.

(FIG. 4A) The PDZ domain of nNOS (amino acids 20–100) is sufficient for binding to CAPON. Truncations of nNOS were subcloned into the Gal4 BD vector and nNOS/CAPON interactions were detected by b-galactosidase assays.

(FIG. 4B) The C-terminal 13 amino acids of CAPON are sufficient for binding to nNOS. Various GST-CAPON fusion proteins were incubated with HEK293 lysates containing nNOS. A CAPON fusion protein comprising the last 100 amino acids binds nNOS, as do fusion proteins comprising the last 13 or 20 amino acids of CAPON. A CAPON fusion protein with the last 20 amino acids deleted no longer binds nNOS. Neither of the control proteins, GST or GST-14-3-3, are able to bind nNOS.

(FIG. 4C) Amino acid substitutions in the C-terminus of CAPON prevent it from interacting with nNOS. $His_6$-fusion proteins of the last 100 amino acids of CAPON were generated and incubated with GST-NOS (1–100) immobilized on glutathione agarose. While the unmutagenized sequence binds (last four amino acids EIAV), mutation of the terminal valine (EIAA) or the penultimate alanine (EIDV) prevents binding. Serine or alanine mutations are tolerated at the n-2 position (ESAV and EAAV), but truncation of the C-terminal 13 amino acids blocks binding altogether.

(FIG. 5A) $His_6$-CAPON fusion proteins specifically block the nNOS/PSD95 interaction in vitro. The C-terminal 100 amino acids were fused to a His6 tag and added to HEK293 lysates transfected with nNOS expression plasmids at the indicated fusion protein concentration. This mixture was added to GST-PSD95 (amino acids 20–364) or GST-PSD93 (116–421), the regions of these proteins previously shown to interact with nNOS (Brenrman et al., 1996). The disruption of the nNOS/PSD95 interaction required the C-terminal 13 amino acids, as this fusion protein (DC20) fails to block the interaction even at 5 mM. Other control proteins such as $His_6$-PIN or $His_6$-FKBP do not disrupt the nNOS-PSD95 interaction.

(FIG. 5B) Quantification of CAPON inhibition of the nNOS/PSD95 interaction. HEK293 cells were transfected with nNOS expression plasmids and then metabolically labeled with [$^{35}$S] methionine. Radiolabeled nNOS was purified and mixed with $His_6$-CAPON as in (A), above. Bound nNOS was resolved by electrophoresis and counts were determined on a PhosphoImager.

Figure 6:
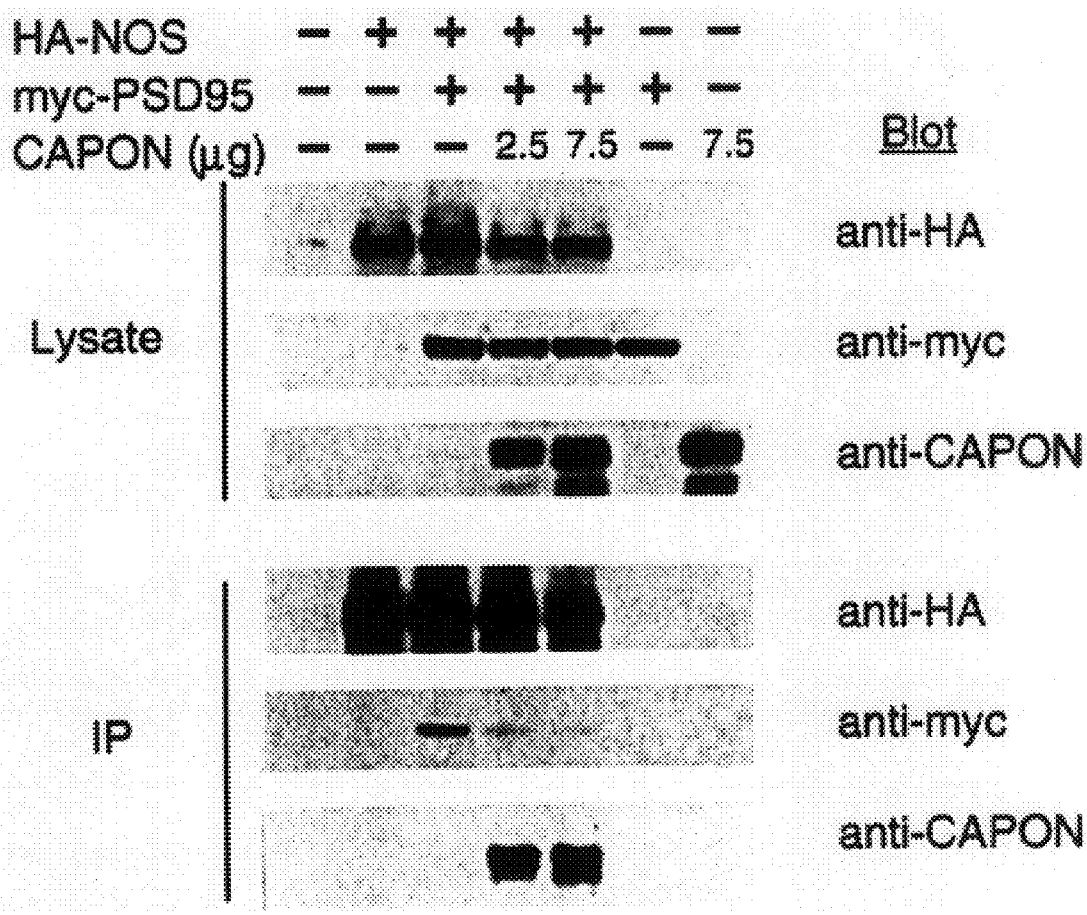

FIG. 6. CAPON expression prevents the interaction of PSD95 and nNOS. HEK293 cells were transfected with various combinations of expression plasmids for HA-tagged nNOS (HA-NOS), myc-tagged PSD95, or CAPON. Following transfection, the lysates were immunoprecipitated with an anti-HA antibody and bound proteins were detected with the appropriate antibodies. Following cotransfection of HA-NOS and myc-PSD95, myc-PSD95 is detected in anti-HA immunoprecipitates. Cotransfection of a full-length CAPON expression plasmid substantially reduces the amount of myc-PSD95 in anti-HA precipitates. In the absence of HA-nNOS transfection, neither myc-PSD95 or CAPON is immunoprecipitated by anti-HA antibodies.

Figure 7:
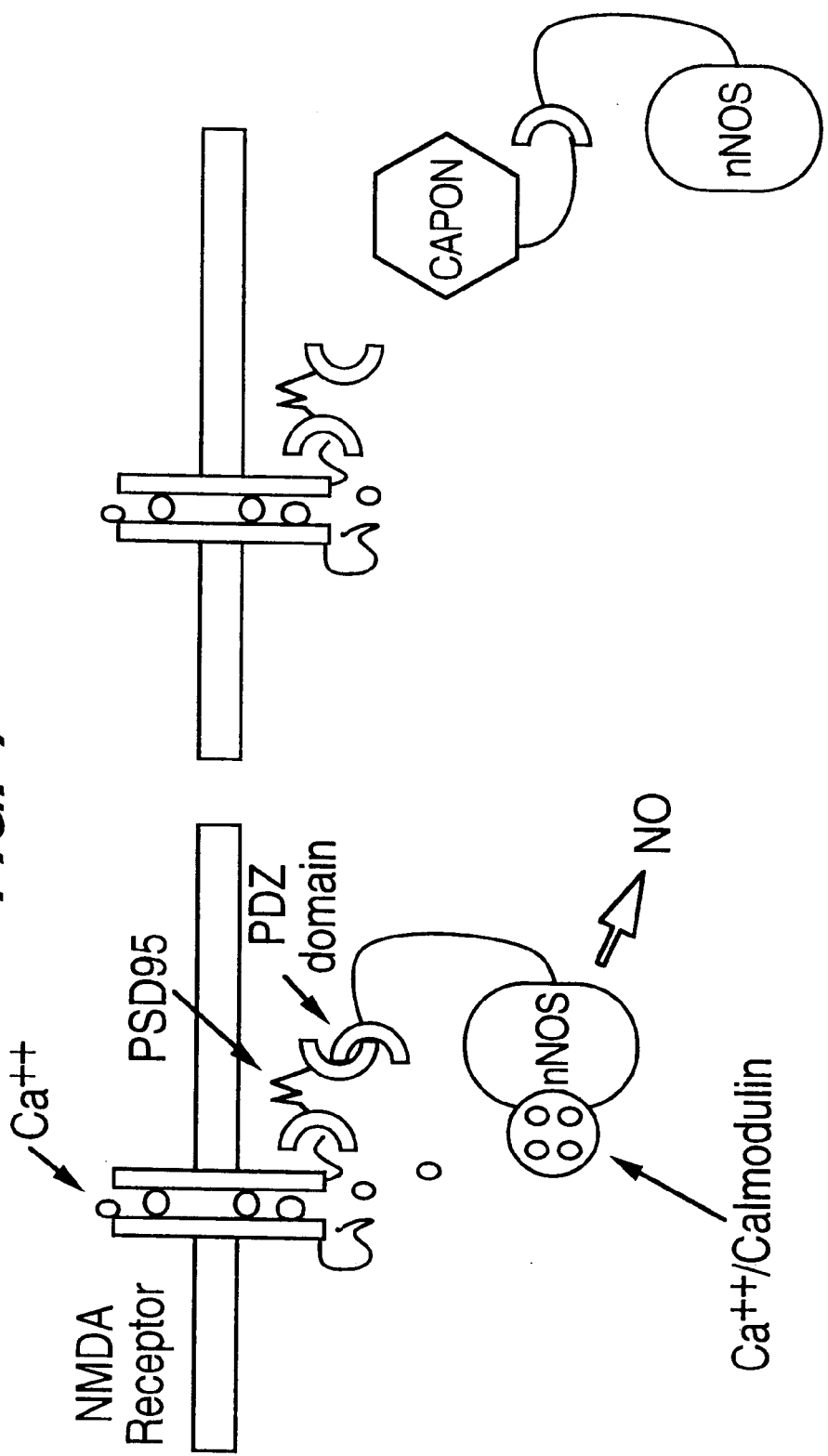

FIG. 7. Model of PSD95/nNOS regulation by CAPON.

NMDA receptors are coupled to nNOS through a PSD95 multimer. These interactions are mediated by PDZ domains. In this complex, nNOS is situated close to NMDA receptor-modulated calcium influx (left). Binding of CAPON (right) results in a reduction of NMDA receptor/PSD95/nNOS complexes, leading to decreased access to NMDA receptor-gated calcium influx and a catalytically inactive enzyme.

DETAILED DESCRIPTION OF THE PREFERRED EMBODIMENTS

We conducted a yeast two-hybrid screen in which we have identified a novel protein which we designate CAPON (Carboxyl-terminal PDZ ligand of nNOS). CAPON is a cytoplasmic protein whose carboxyl terminus binds to the PDZ domain of nNOS. CAPON competes with PSD95 and PSD93 for binding to nNOS and thus may participate in the translocation and impede the activation of this enzyme.

It is a discovery of the present invention that the mammalian protein Capon (Carboxy-terminal PDZ ligand of nNOS) physically interacts with and inhibits the activity of neuronal nitric oxide synthase (nNOS). Although it was known that nNOS regulates the release of its product, the messenger molecule nitric oxide, all of the proteins involved in its cellular localization were previously unknown.

Mammalian Capon protein has the sequence disclosed in SEQ ID NO:2 or 4, or other sequences which are at least about 80, 85, 87, 89, or 90% identical. Any biologically active variants of this sequence that may occur in mammalian tissues are within the scope of this invention. Biologically active variants bind to and inhibit nNOS binding to PSD95 and PSD93. Mammalian Capon proteins may comprise amino acids 1–503 as shown in SEQ ID NO:2 or 1–156 as shown in SEQ ID NO: 4. Fragments of a mammalian Capon protein, comprising at least eight, nine, ten, twelve, thirteen, or sixteen consecutive amino acids selected from the sequence shown in SEQ ID NO:2 or 4, may also be used. Such fragments may be useful, for example, in various assays, as immunogens, or in therapeutic compositions. They may also be used as preparative reagents for purifying nNOS. A fusion protein may also be used for many of these purposes, including as a reagent and as an immunogen.

A fusion protein consists of a full length mammalian Capon protein or a Capon protein fragment fused to a second protein or protein fragment by means of a peptide bond. The second protein or protein fragment may be, for example, a ligand for yet a third molecule. The second protein or protein fragment may be labeled with a detectable marker or may be an enzyme that will generate a detectable product. A fusion protein may be useful, for example, to target full-length Capon protein or a Capon fragment comprising one or more specific domains, to a specific location in a cell or tissue.

Any of these Capon-related proteins may be produced by expressing Capon cDNA sequences in prokaryotic or eukaryotic host cells, using known expression vectors. Synthetic chemistry methods can also be used to synthesize Capon protein, fusion protein, or fragments. Alternatively, Capon protein can be extracted, using standard biochemical methods, from Capon-producing mammalian cells, such as brain cells. The source of the cells may be any mammalian tissue that produces Capon protein including human, rat, or mouse. Methods of protein purification, such as size exclusion chromatography, ammonium sulfate fractionation, ion exchange chromatography, affinity chromatography, or preparative gel electrophoresis, are well known in the art. Given the sequences disclosed in SEQ ID NO:2 and 4, an ordinary artisan can readily select appropriate methods to obtain a preparation of mammalian Capon protein that is substantially free from other mammalian proteins. An isolated Capon protein is purified from other compounds that may normally associate with Capon protein in a cell, such as certain proteins, carbohydrates, lipids, or subcellular organelles.

The present invention also provides a preparation of antibodies that specifically bind to mammalian Capon protein. The antibodies may be polyclonal or monoclonal and may be raised against biochemically isolated, chemically synthesized, or recombinantly produced full-length Capon protein, Capon protein fragments, or Capon fusion proteins. Techniques for raising antibodies directed against intracellular proteins such as mammalian Capon are well known in the art. The antibodies bind specifically to Capon epitopes, preferably epitopes not present on other mammalian proteins. Antibodies that bind specifically to Capon proteins include those that bind to full-length Capon protein, Capon fragments or degradation products, as weak as to alternatively spliced forms of Capon proteins, or to Capon fusion proteins. In preferred embodiments of the invention the antibodies prevent Capon binding to nNOS, immunoprecipitate Capon protein from solution, and react with Capon protein on Western blots of polyacrylamide gels. Preferably the antibodies do not exhibit nonspecific cross-reactivity with other mammalian proteins on Western blots or in immunocytochemical assays. Techniques for purifying Capon antibodies are those which are available in the art. In a more preferred embodiment, antibodies are affinity purified by passing antiserum over a support column to which Capon protein is bound and then eluting the bound antibody, for example with high salt concentrations. Any such techniques may be chosen to achieve the preparation of the invention.

The polynucleotides of the present invention encode Capon protein. These polynucleotides may be isolated and purified free from other nucleotide sequences by standard purification techniques, using restriction enzymes to isolate fragments comprising the Capon encoding sequences. The polynucleotide molecules are preferably intron-free and have the sequence shown in SEQ ID NO:1 or 3. Such Capon cDNA molecules can be made inter alia by using reverse transcriptase with Capon mRNA as a template. The polynucleotide molecules of the invention can also be made using the techniques of synthetic chemistry given the sequence disclosed herein. The degeneracy of the genetic code permits alternate nucleotide sequences to be synthesized that will encode the Capon amino acid sequence shown in SEQ ID NO:2 or 4. All such nucleotide sequences are within the scope of the present invention, as well as those which are at least 70, 75, 80, 85, or 90% identical. The Capon polynucleotide molecules can be propagated in vectors and cell lines as is known in the art. The constructs may be on linear or circular molecules. They may be on autonomously replicating molecules or on molecules without replication sequences. Recombinant host cells can be formed by introducing the genetic constructs of the present invention into cells. Any of those techniques which are available in the art can be used to introduce genetic constructs into the cells. These include, but are not limited to, transfection with naked or encapsulated nucleic acids, cellular fusion, protoplast fusion, viral infection, and electroporation. Introduction of genetic constructs may be carried out in vitro or in vivo.

The invention also provides a recombinant DNA construct for expressing Capon antisense nucleic acids. The construct contains a promoter and a coding sequence for Capon consisting of at least 12 and preferably at least 15 or 20 contiguous base pairs selected from SEQ ID NO:1 or 3. The Capon coding sequence is in an inverted orientation with respect to the promoter, so that when the sequence is transcribed from the promoter, an RNA complementary to native Capon-encoding mRNA is produced. The construct may also include a terminator at the 3' end of the inverted Capon coding sequence. The antisense molecules produced using the DNA construct of the invention may be used to decrease or prevent the transcription of Capon mRNA. The antisense molecules may be used in vitro or in vivo, as pharmacological agents for the purpose of influencing nNOS activity.

According to the present invention, nNOS is inhibited by mammalian Capon protein, which competes with PSD95 and PSD93 for binding to nNOS, thereby inhibiting nNOS activity. Suitable inhibitory concentrations range from 1 nM to 1 mM. In a preferred embodiment the concentration of Capon protein is at least 250 nM. In a more preferred embodiment the concentration of Capon protein is at least 1 $\mu$M. Greater concentrations of Capon protein may also be used. nNOS activity may be measured, for example, by assaying nitric oxide-dependent cGMP formation in HEK 293 cells cotransfected with DNA encoding Capon and nNOS. Other cell lines, such as mouse N1E-115 neuroblastoma cells, may be used as well. Formation of cGMP may be measured, for example, by radioimmunoassay or by spectrophotometry. nNOS activity may be measured in intact cells or in cell lysates. Other assays for measuring nNOS activity may also be used. NO or citrulline can also be measured.

The present invention also provides methods of screening test compounds for the ability to decrease or augment nNOS activity. The test compounds may be pharmacologic agents already known in the art or may be compounds previously unknown to have any pharmacological activity. The compounds may be naturally occurring or designed in the laboratory. They may be isolated from microorganisms, animals, or plants, and may be produced recombinantly, or synthesized by chemical methods known in the art. A test compound can be contacted with a mixture of mammalian Capon protein (or the NOS-binding portion thereof) and a polypeptide containing an nNOS PDZ domain which is a contiguous sequence selected from the N-terminal about 100 amino acids of nNOS amino acid sequences as shown in SEQ ID NO:5 and 6. Analogous domains in other mammalian nNOS proteins can also be used. These are referred to as biologically active, naturally occurring variants of the rat or human protein. These molecules may be produced recombinantly or may be synthesized using standard chemical methods. The nNOS or Capon binding partner may consist of less than the entire nNOS. The two binding partners may be prebound prior to the step of contacting with the test compound. Alternatively, the test compound may contact one of the binding partners before the second binding partner is added. The PDZ domain-containing molecule may be in solution or may be bound to a solid support. These molecules may be unlabeled or labeled, for example, with a radioactive, fluorescent, or other detectable marker. They may be fusion proteins comprising a nNOS PDZ domain and another protein with or without a detectable enzymatic activity. The amount of at least one of the two binding partners that is bound or unbound in the presence of the test compound is then measured. A number of methods may be used to measure the amount of bound molecules. For example, the relative concentration of bound to unbound may be detected by examining the apparent molecular masses of the molecules by size exclusion chromatography or by polyacrylamide gel electrophoresis under non-reducing conditions. Other methods of measuring binding or dissociation of the molecules will readily occur to those of ordinary skill in the art and can be used. A test compound that decreases the amount of the polypeptide and Capon that are bound is a potential drug for increasing nNOS activity. A test compound that increases the amount of the polypeptide and Capon that are bound is a potential drug for decreasing nNOS activity.

According to the present invention a method is also provided of using the yeast two-hybrid technique to screen for test compounds that decrease or augment nNOS activity. The yeast two-hybrid technique is generically taught in Fields, S. and Song, O., *Nature* 340, 245–46, 1989. In a preferred embodiment, a cell is contacted with a test compound. The cell comprises a first fusion protein comprising a DNA binding domain and all or a portion of a mammalian Capon protein consisting of a contiguous sequence of amino acids selected from the amino acid sequence shown in SEQ ID NO:2 and capable of binding to nNOS (this typically requires the 13 carboxy terminal amino acids). The cell also comprises a second fusion protein comprising a transcriptional activating domain and all or a portion of nNOS, wherein the portion comprises a contiguous sequence of amino acids selected from amino acids 14–89 as shown in SEQ ID NO:5 or 6 or naturally occurring biologically active variants thereof. Alternatively, the DNA binding domain and the transcriptional activating domains can be paired with the opposite proteins. The interaction of the portion of the Capon protein with the portion of nNOS reconstitutes a sequence specific transcriptional activating factor. A reporter gene is also present in the cell. The reporter gene comprises a DNA sequence to which the DNA binding domain of the first fusion protein specifically binds. When the Capon and nNOS regions are bound together, the DNA binding domain and the transcriptional activating domain will be in close enough proximity to reconstitute a transcriptional activator capable of initiating transcription of a detectable reporter gene in the cell. The expression of the reporter gene in the presence of the test compound is then measured. A test compound that increases the expression of the reporter gene is a potential drug for decreasing nNOS activity. A test compound that decreases the expression of the reporter gene is a potential drug for augmenting nNOS activity. Test compounds which increase nNOS activity are potential drugs for modulating aggressive behaviour, particularly aggressive sexual behavior. Test compounds which decrease nNOS activity are potential drugs for treating stroke patients and other neuronal degeneration which is mediated by NO.

Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16 (See, e.g., G. J. Hannon et al., *Genes Dev.* 7, 2378, 1993; A. S. Zervos et al., *Cell* 72, 223, 1993; A. B. Votjet et al., *Cell* 74, 205, 1993; J. W. Harper et al., *Cell* 75, 805, 1993; B. Le Douarin et al., *Nucl. Acids Res.* 23, 876, 1995). A number of plasmids known in the art can be constructed to contain the coding sequences for the fusion proteins using standard laboratory techniques for manipulating DNA (see, e.g., Example 1, below). Suitable detectable reporter genes include the *E. coli* lacZ gene, whose expression may be measured colorimetrically (see, e.g., Fields and Song, supra), and yeast selectable genes such as HIS3 (Harper et al., supra; Votjet et al., supra; Hannon et aL, supra) or URA3 (Le Douarin et al., supra). Methods for transforming cells are also well known in the art. See, e.g., A. Hinnen et al., *Proc. Natl. Acad. Sci. U.S.A.* 75, 1929–1933, 1978. The test compound may comprise part of the cell culture medium or it may be added separately. The tester cell need not be a yeast cell, but may be a bacterial, other fungal, or mammalian cell.

In another embodiment, a cell is contacted with a test compound. In this embodiment, the cell comprises (i) a first expression vector comprising a subgenomic polynucleotide encoding nNOS or a naturally occurring biologically active variant thereof, and (ii) a second expression vector comprising a subgenomic polynucleotide encoding a portion of Capon or a naturally occurring biologically active variant thereof The portion of Capon is capable of binding to nNOS. NO production by the cell is then measured, for example by radioimmunoassay or by spectrophotometry. A test compound that increases the amount of NO produced by the cell is a potential drug for augmenting nNOS activity. A test compound that decreases the amount of NO in the cell is a potential drug for decreasing nNOS activity. NO production may be determined by assaying for cGMP or citrulline as well. A test compound which binds to nNOS at the Capon binding site may either inhibit Capon binding, thus favoring the interaction of nNOS and PSD95 or mimic Capon thus inhibiting the interaction of nNOS and PSD95.

Because expansion of glutamine repeats has been shown to be associated with neurodegenerative and other neurological diseases, the glutamine repeat in Capon is believed to be relevant to pathogenesis. Thus either the Capon protein or the gene encoding it can be examined for the number of glutamine residues in the glutamine repeat region, or the number of glutamine codons (CAG) in the CAG repeat region of the gene. Expansion to a number greater than 6 indicates a propensity for or the presence of a neurological disease, likely a neurodegenerative disease. As in other examples where this mechanism has been demonstrated, the degree of expansion is associated with the severity of disease. It is likely that the glutamine repeat region interacts with a binding partner, and the avidity of the inteaction is governed by the degree of expansion of the glutamine repeats. Any means for determining the sequence of a gene or protein may be used, including but not limited to direct sequencing, hybridization with allele-specific probes, binding to antibodies, size determination on gel electrophoresis.

The main finding of this study is the identification of a novel protein, CAPON, which interacts selectively with nNOS. The interaction of CAPON with nNOS is highly specific and has been verified by several methods of monitoring protein-protein interactions. The similarities in neuronal localizations of CAPON and nNOS imply that these proteins interact physiologically and that the principal biological function of CAPON may be to interact with nNOS. The apparent selectivity of this interaction contrasts with other nNOS binding proteins such as PSD95, PIN and calmodulin, each of which bind to multiple other proteins.

The competitive binding for nNOS by CAPON and PSD95 suggests a model for regulating the translocation of nNOS between cytoplasm and synaptic structures (FIG. 7). Presumably, NO release into the synaptic space must be preceded by its translocation to synaptic structures by binding to PSD95. We propose that this process can be blocked by CAPONs removal of nNOS from PSD95, and translocating nNOS into the cytoplasm, or some other cellular compartment. In this manner CAPON could lead to effective nNOS inhibition. Although CAPON does not inhibit nNOS catalytic activity directly (data not shown), CAPON would reduce the accessibility of nNOS to NMDA receptor-mediated calcium influx, thus diminishing the capacity of nNOS to exert its physiologic or pathologic effects. Small molecules which specifically bind to nNOS in a manner similar to that of CAPON are useful for blocking NO-mediated neuronal degeneration.

We have explored potential mechanisms that might regulate the nNOS/CAPON interaction. For instance, we phosphorylated nNOS in transfected HEK 293 cells by treatment with forskolin, phorbol esters, dibutyryl cyclic AMP and 8-bromo-cyclic GMP and in vitro or with purified nNOS protein utilizing protein kinase C, protein kinase A and calcium calmodulin dependent protein kinase using methods described previously (Bredt et al., 1992). We have been unable to alter CAPON-nNOS interactions by any of these treatments.

Conceivably, phosphorylation of CAPON regulates its interactions with nNOS. Recently some of us showed that phosphorylation of the n-2 serine in the potassium channel BIRK-2 regulates its binding to a PDZ domain in PSD95 (Cohen et al., 1996). CAPON, and several other PDZ-domain ligands (Songyang et al., 1997), lack a serine in this position and so must be regulated in some other manner. One possible mechanism may be a regulation of the ligand's C-terminal secondary structure. A recent crystallographic study of a PDZ domain complexed with a short cognate peptide shows that the peptide binds in an antiparallel beta-sheet conformation, with characteristic beta-sheet contacts between the peptide and a strand of a beta-sheet within the PDZ domain (see Doyle et al., 1996). In a physiologic setting, the unbound cognate sequence may constitutively adopt a beta-sheet conformation, with the other beta-strands coming from other, possibly distant, residues within the ligand protein's sequence. This beta-sheet might constitute an endogenous high-affinity ligand. This notion is supported by our observation that short, presumably unfolded, peptides comprising the C-terminal nine residues of CAPON bind nNOS weakly, while 16-residue peptides are more potent competitors ($IC_{50}$=10 mM), although both are much less effective than 100 amino acid fusion proteins which are active in the nanomolar range (see FIG. 5). Peptide competitors that interact with other PDZ domains have also been utilized at 10 and 500 mM concentrations (see Brenman et al., 1996; Kornau et al., 1995). Conceivably, the nNOS-CAPON interaction would be disrupted simply by disrupting the beta-sheet conformation of the C-terminus, which might be achieved by phosphorylation at a distance.

The nNOS PDZ domain is the first example of a PDZ domain which binds to other PDZ domains. The region of nNOS which possesses this property is the PDZ domain plus the adjacent ~50 amino acids on the carboxyl-side of the PDZ domain (residues 1–150) (Brenman et al., 1996). The additional amino acids in this super-sized PDZ domain may by required to accomodate larger ligands such as other PDZ domains. The finding in this report of another physiologic ligand for the PDZ domain, namely, the C-terminal region of CAPON, raises the question of whether the same or different portions of the nNOS PDZ domain account for the binding to two seemingly different ligands. Because these interactions are mutually exclusive, it is likely that the ligand-binding cleft in the PDZ domain mediates both interactions. Previously identified proteins which contain C-terminal PDZ-binding sequences have been membrane associated. By contrast, CAPON is soluble. This demonstrates that PDZ domains may mediate purely cytosolic protein-protein interactions.

Stricker et al. (1997) recently characterized the specificity of the nNOS PDZ-binding domain. These researchers used a phage display method to identify NOS-binding peptides. Peptides ending in the sequence aspartate-X-valine were found to be high affinity ligands. Interestingly, unlike CAPON, these peptides did not bind the canonical nNOS PDZ domain (amino acids 13–89) but bound the extended PDZ domain only (amino acids 1–150). This extended domain is the minimal sequence which mediates PDZ-PDZ interactions. Presumably the differences in the binding sites in nNOS for the phage display peptide and CAPON account for the differences between the sequence specificity requirements for PDZ-PDZ interactions and PDZ-CAPON interactions.

The following are provided for exemplification purposes only and are not intended to limit the scope of the invention which has been described in broad terms above.

EXAMPLE 1.

Identification and Cloning of CAPON

Figure 1A:
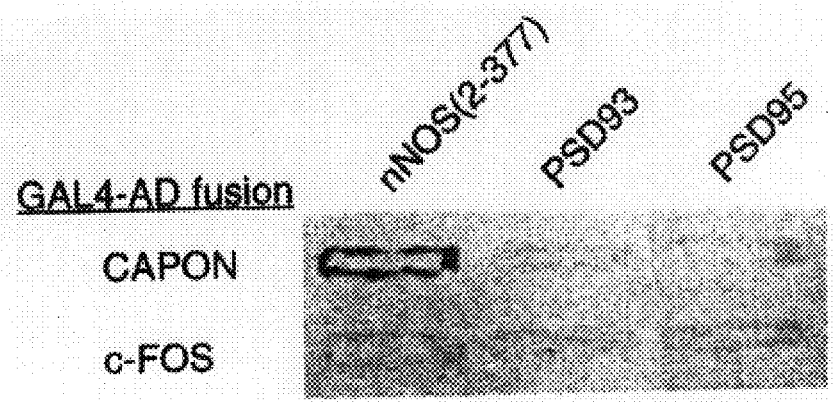

We conducted a yeast two-hybrid screen employing the first 377 amino acids of nNOS, a region which includes the PDZ domain that comprises the first 100 amino acids of nNOS. Screening of six million clones resulted in the identification of three distinct cDNA inserts, one of which, PIN, has been previously reported (Jaffrey and Snyder, 1996) while the other two are overlapping cDNAs derived from a gene which is designated CAPON. The CAPON two-hybrid clones share a common carboxyl terminus and are predicted to translate into 125 and 327 amino acid peptides followed by a stop codon. The 125 amino acid C-terminal fragment of CAPON specifically interacts with nNOS in the two-hybrid system as is evident from the failure of CAPON to interact with fragments of PSD93 and PSD95 containing PDZ domains (FIG. 1A). Moreover, nNOS fails to interact with another control protein, c-fos. To obtain a full-length CAPON cDNA, we screened a rat brain cDNA library with the larger two-hybrid clone and isolated a 2100 bp cDNA which overlapped with the two-hybrid clone and was used to assemble a final 2820 bp cDNA (see Methods). The conceptual translation of this cDNA produces a 503 amino acid protein (FIG. 1B SEQ ID NO:4). The first ATG in the cDNA was 393 bp from the 5' end of the cDNA and was situated in a context that conformed to the Kozak consensus sequence for an initiator methionine (Kozak, 1991).

CAPON displays no significant homology to any other known class of protein except for an N-terminal 145 amino acid stretch of amino acids which has residues suggestive of a phosphotyrosine-binding (PTB) domain (Zhou et al., 1995). CAPON's PTB domain most closely resembles the mouse numb protein's PTB domain (Zhong et al., 1996) with nearly 28% sequence identity on this region. The similarity between CAPON and numb are limited to this domain. PTB domains are targetted to phosphotyrosine containing proteins such as growth factor receptors (reviewed in van der Geer and Pawson, 1995).

Outside of the PTB domain, CAPON lacks any well known consensus sequences except for an 18 nucleotide stretch of CAG repeats that corresponds to six glutamines. Glutamine repeats occur in proteins whose expansion results in neurodegenerative diseases as exemplified by huntingtin, the protein which is altered in Huntington's disease (Ross, 1995). A BLAST search (Altschul et al., 1990) of an expressed sequence-tag database, dBEST, reveals a human brain-derived EST with ~75% nucleotide identity to CAPON. The cDNA insert was 1.4 kb and corresponds to the C-terminal 156 amino acids of CAPON plus one kb of 3' UTR. The conceptual translation of this portion of human CAPON has 92% amino acid identity with the rat protein (FIG. 1B).

Figure 1C:
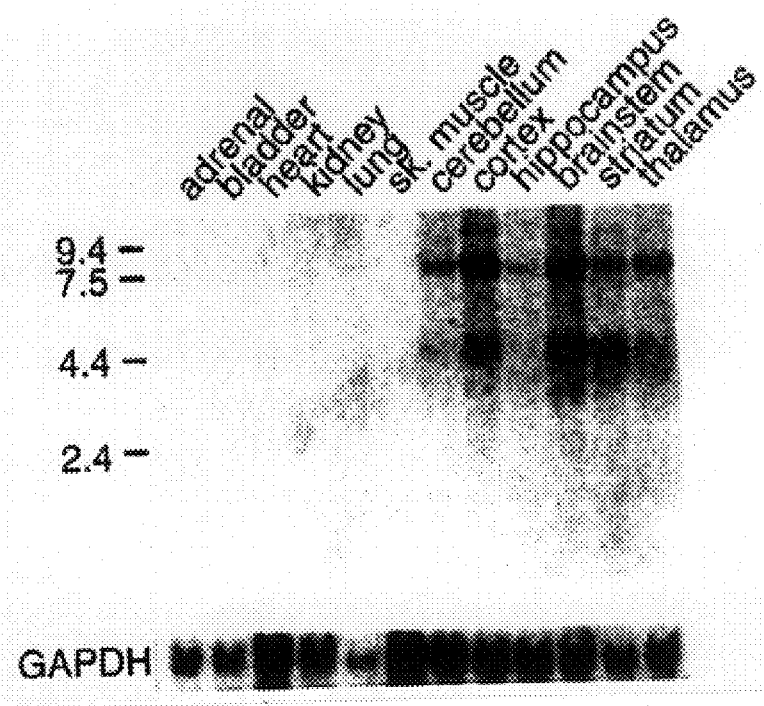

Northern (RNA) blotting reveals a predominant 7.5 kb transcript which is detected only in brain regions with no expression evident in adrenal, bladder, heart, kidney, lung and skeletal muscle (FIG. 1C). Marked regional variations occur in the brain with highest densities in the cerebral cortex and medulla-oblongata and lowest levels in the hippocampus.

Figure 2E:
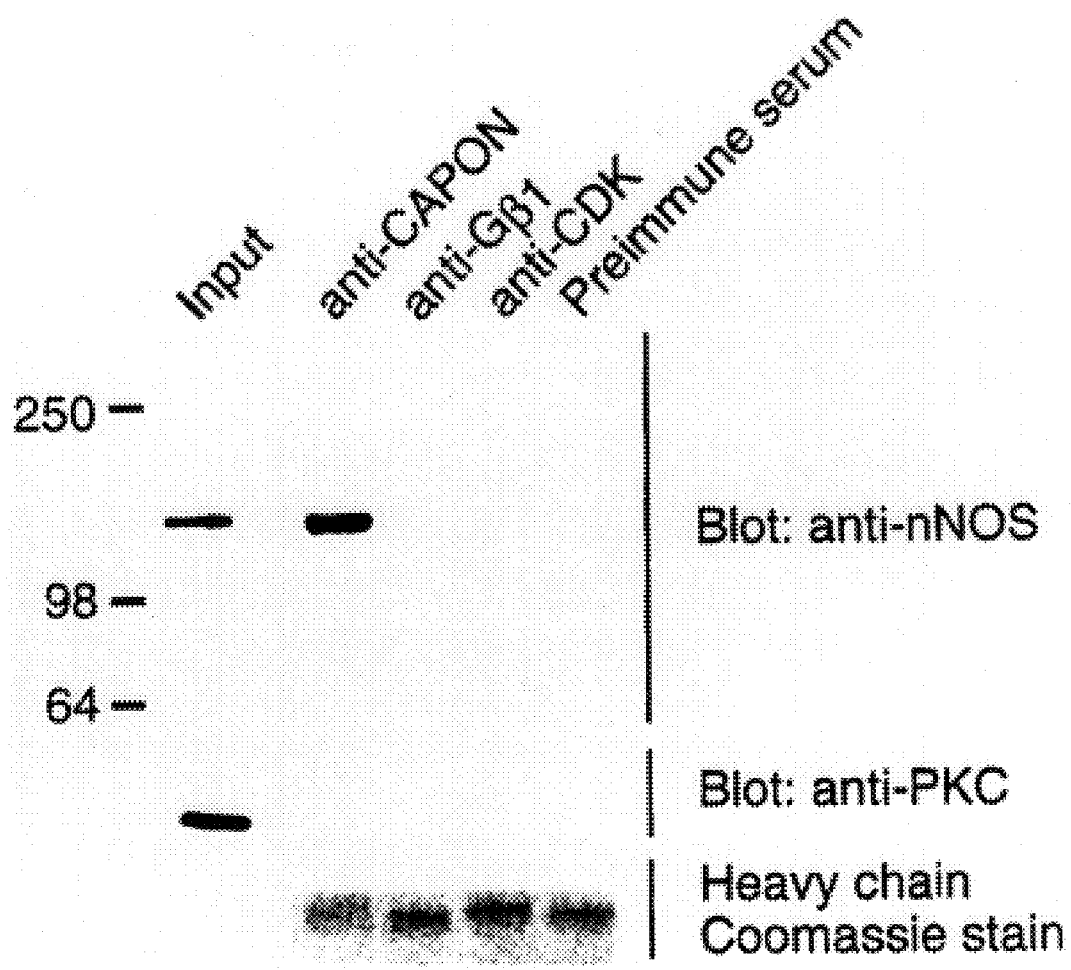
Figure 3A:
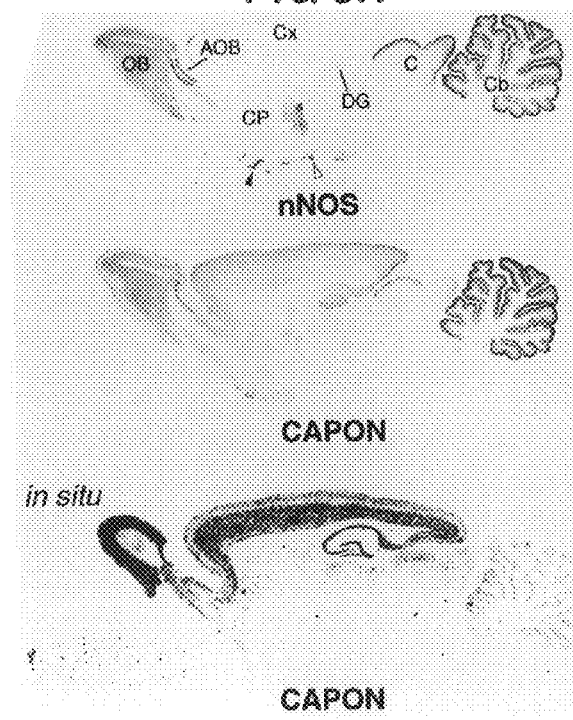
FIGS. 3A and 3B. Immunohistochemical localization of nNOS and CAPON.
Figure 3B:
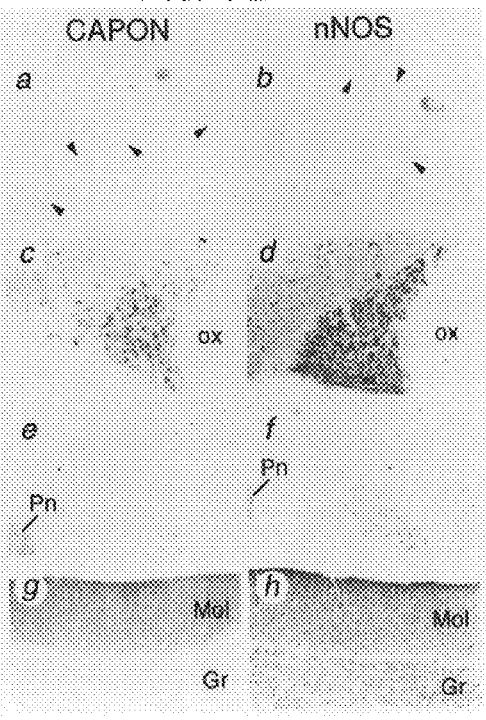

To assess the specificity of interactions between CAPON and nNOS, we evaluated the binding of a GST-CAPON fusion protein, consisting of C-terminal 125 amino acids of CAPON, with nNOS, eNOS and inducible NOS (iNOS) (FIG. 2A). Lysates of HEK-293 cells transfected with expression plasmids for each of the three forms of NOS were incubated with GST-CAPON. After extensive washing of the resin, bound nNOS was detected by Western blotting with the appropriate isoform-specific antibody. nNOS interacts strongly with GST-CAPON, while eNOS and iNOS do not interact. No interactions are evident with the GST control.

We also examined interactions of CAPON and nNOS by utilizing a GST-fusion protein of the $NH_3$-terminal 100 amino acids of nNOS, the PDZ domain. Following incubation with cerebellar lysates the washed GST-nNOS resin was subjected to SDS-PAGE and Western blotted with a purified antibody directed against the C-terminal 125 amino acids of CAPON. A single band corresponding to CAPON is detected, while no CAPON is bound to the GST control. A lower molecular weight band in homogenates is occasionally detected using our anti-CAPON antibodies. This protein fails to interact with GST-nNOS fusion proteins (FIG. 2B) and may represent an unrelated cross-reactive protein, or the product of an alternatively spliced CAPON mRNA which fails to bind nNOS.

The protein-protein interactions we detected with cell lysates and GST-fusion proteins might have reflected a tertiary interaction between nNOS, an unidentified protein and CAPON. To determine if CAPON directly binds to nNOS, we conducted blot overlay experiments (FIG. 2C). Lysates of HEK 293 cells transfected with nNOS were resolved on a polyacrylamide gel, transferred to nitrocellulose and then probed with [$^{32}$P]GST-CAPON. The radiolabeled CAPON probe binds to a single 160 kD band comigrating with a nNOS standard, while no binding is evident in mock transfected cells, demonstrating that CAPON physically interacts in a direct manner with nNOS.

To ascertain if complexes of CAPON and nNOS exist physiologically, we used two approaches. Our first approach took advantage of a NOS-affinity resin consisting of 2', 5'-ADP ribose crosslinked to an agarose matrix. This resin has been used previously to purify nNOS from cerebellar supernatants (Bredt and Snyder, 1990). Following incubation with cerebellar supernatants, the resin and washed extensively. As expected, a significant portion of the nNOS found in the starting material was bound to the resin (FIG. 2D). To determine if nNOS and CAPON were physiologically associated, we next assayed for CAPON bound to the resin. Like nNOS, CAPON was substantially enriched in the bound fraction. As a control we assayed for the resin-binding ability of CAPON from supernatants derived from mice with a genomic deletion of nNOS. These mice express a truncated version of nNOS which lacks the PDZ domain and is unable to bind CAPON. Substantially less CAPON in these supernatants bound to the 2', 5'-ADP ribose resin indicating that CAPON has negligible intrinsic affinity for the resin and that CAPON-binding in wild-type supernatants was due to nNOS. The smaller cross-reactive band was also enriched on this resin, supporting the notion that it is in some manner related to CAPON by alternative splicing or proteolytic degradation. Interestingly, the total level of CAPON in knockout supernatants was approximately one half that in wild-type mice, possibly due to the absence of a stabilizing effect of nNOS.

As a second approach, we immunoprecipitated CAPON from cerebellar supernatants and assayed for nNOS by Western blot (FIG. 2E). nNOS coprecipitates with anti-CAPON antibodies but is not detected in immunoprecipitates generated using preimmune serume, an antibody to the G-protein subunit β1, or with an antibody to cyclin-dependent kinase 2. To determine if the enrichment observed in anti-CAPON immunoprecipitates was specific, we asked if a control protein, protein kinase C-β I/II, was similarly enriched in these fractions, We found that this protein was absent in all of the precipitates (FIG. 2E) indicating that the coprecipitation of nNOS with CAPON was specific. These two approaches support the notion that CAPON and NOS exist as a complex in the rat cerebellum.

In other experiments we metabolically labeled N1E-115 mouse neuroblastoma cells with [$^{35}$S] methionine and examined for the presence of proteins that would bind to GST-CAPON. The only protein that specifically interacted with CAPON is a 160 kD) protein that comigrates with an nNOS standard (unpublished observations), suggesting that nNOS is the most abundant CAPON-binding protein in these cells.

General Methods and Materials

Molecular biology reagents were from New England Biolabs (Beverly, Mass.) and all other reagents were from Sigma (St. Louis, Mo.) except as indicated. Protein concentrations were determined by Bradford assay.

Yeast Two-Hybrid Methods

Two-hybrid screens and the construction of the parent vectors pPC86, containing the GAL4-activation domain, and pPC97, containing the GAL4-DNA binding domain, have been described (Jaffrey and Snyder, 1996). Plasmid pBD-NOS(2–377) was prepared by the insertion of an nNOS PCR product corresponding to amino acids 2–377 of rat nNOS into the Sal I and Bgl II sites of pPC97, resulting in an open reading frame encoding a GAL4 BD-NOS fusion protein (Jaffrey and Snyder, 1996). The nNOS fragment was constructed by PCR using the following primers: 5'-GACTAGTCGACTGAAGAGAACACGTTTGGG-3' (coding strand, SEQ ID NO: 7) and 5'-TCTGCAGATCTCAGTGGGCCTTGGAGCCAAA-3' (noncoding strand. SEQ ID NO: 8).

A rat hippocampal cDNA library in pPC86 (Li et al., 1995) was amplified once in DH10B (Gibco BRL) as described (Jaffrey and Snyder, 1996) and transformed into yeast containing the pBD-NOS(2–377) plasmid. pAD-CAPON1 and pAD-CAPON2 were identified as 0.8 kb and 1.9 kB clones, respectively, that activated lacZ transcription and conferred histidine prototrophy in the presence of pBD-NOS(2–377). Plasmids were sequenced by automated fluorescent sequencing of both strands. Yeast two-hybrid vectors containing the second PDZ domain of PSD93 (amino acids 116–421) and the three PDZ domains of PSD95 (amino acids 20–364) have been described previously (Brenman et al., 1996).

Truncated NOS fragments comprising amino acids 2–165 and 2–284 were generated by restriction of the initial NOS (2–377) PCR fragment with Nco I and Ava I, respectively followed by Klenow-filling in of that end and ligation into pPC97. Other truncated NOS fragments were prepared by PCR and have been described (Jaffrey and Snyder, 1996).

cDNA cloning of CAPON

A CAPON DNA probe was generated by the random hexamer method using the pAD-CAPON2 cDNA as a template. This probe was used to screen a rat brain lamdaZAP II cDNA library (Stratagene) using methods described by the manufacturer. A 2.1 kb cDNA was isolated which overlapped with the pAD-CAPON2 clone. The cDNAs were ligated at an overlapping Xba I site to produce the full-length 2,812 bp cDNA and subcloned into pCMV for eukaryotic expression. The human CAPON EST was the sole CAPON homolog identified in a BLAST seacrh (Altschul et al., 1990). I.M.A.G.E. consortium (http://www-bio.llnl.gov/bbrp/image/image.html/) clone 34183 (Lennon et al., 1996) was purchased from Research Genetics (Huntsville, AL.).

RNA (Northern) Blotting

Thirty micrograms of whole RNA were isolated from rat tissues using the Triazol reagent (Gibco BRL) and separated on agarose-formaldehyde gels. RNA was transferred to Hybond N+membranes (Amersham) and a DNA probe, generated using the random hexamer method with the two-hybrid CAPON cDNA as a template, was hybridized in Rapid-hyb buffer (Amersham) overnight at 65° C. The blots were subsequently washed sequentially in 2×SSC with 0.1% SDS, once at room temperature for 15 min, 1×SSC with 1% SDS twice at 65° C., 0.1×SSC with 1% SDS twice at 65° C., and then with 0.1×SSC with 5% SDS twice at 65° C. The blot was apposed to film for 4 days at −80° C. to visualize the bands.

GST-Fusion Protein Binding Assays

GST-fusion proteins were prepared in BL21(DE3) Escherichia coli (Novagen) with glutathione agarose as an affinity resin for purification (Smith and Johnson, 1988), except that bacterial pellets were sonicated in lysis buffer (50 mM Tris-HCl (pH 7.7), 100 mM NaCl, and 2 mM EDTA), supernatants were adjusted to 1% Triton X-100, washes were done in 50 mM Tris-HCl (pH 7.7), 500 mM NaCl, 2 mM EDTA, and 1% Triton X-100, and protein was purified with elution buffer (50 mM tris-HCl (pH 7.7), 100 mM NaCl, 10 mM reduced glutathione, and 2 mM EDTA).

Transfections were performed with 10 μg of each plasmid using the calcium phosphate method. Following transfection, cells were sonicated in buffer A [50 mM Tris-HCl (pH 7.7), 100 mM NaCl, 2 mM EDTA, and 1% Triton X-100] and cleared by centrifugation. This cellular lysate was incubated with GST-fusion protein immobilized on glutathione-agarose for one hour at 4° C. and washed extensively in HNTG buffer [20 mM Hepes (pH 7.4), 500 mM NaCl, 10% glycerol, and 0.1% Triton X-100] five times, for ten minutes per wash at room temperature. A GST-CAPON fusion protein consisting of amino acids 379–503 was used for binding assays because it was was more soluble when expressed in bacteria than larger CAPON fusion proteins.

For quantitative binding experiments, transfected cells were metabolically labeled overnight with 200 mci [$^{35}$S] methionine and nNOS was purified by NADPH elution of 2', 5' ADP ribose as described previously (Bredt and Snyder, 1990).

The material remaining on the resin was eluted with SDS-PAGE sample buffer and nNOS was detected by immunoblot using antibodies specific to each NOS isoform (Transduction Labs). A polyclonal antiserum to CAPON was generated in rabbits by using a His$_6$-tagged CAPON fusion protein. GST-CAPON was crosslinked to glutathione agarose with dimethylpimelimidate and this resin was used to purify CAPON antibody. To confirm the specificity of the antibody, immune serum was incubated with His$_6$-CAPON which results in the abolishment of the signal. Incubation with His$_6$-FKBP has no effect on the signal (data not shown).

For blot-overlay analysis, CAPON was inserted into pGEX-4T2, a derivative of PGEX4T2 in which two cyclic AMP-dependent protein kinase (PKA) sites were inserted between the GST moiety and the multiple cloning site (Jaffrey and Snyder, 1996). Kinase reactions and blot overlays were performed as described (Kavanaugh and Williams, 1994).

EXAMPLE 2.

The C-terminus of CAPON Binds to the PDZ Domain of nNOS

To examine the region of nNOS that binds to CAPON, we conducted yeast two-hybrid experiments with various truncations of nNOS (FIG. 4A). As little as the first 100 amino acids of nNOS binds to the C-terminal 125 amino acids of CAPON. This portion of nNOS contains the full PDZ domain as defined by MacKinnon and associates (Doyle et al., 1996) who identified the PDZ consensus domain in nNOS as amino acids 14–89. Deletion of the first 20 amino acids of nNOS, which includes the first seven amino acids of the PDZ domain, does not abolish binding, but larger NH$_3$-terminal deletions abolish binding, presumably because they result in a loss of important structural components of the PDZ domain. The nNOS construct comprising amino acids 163–245, which represents the PIN-binding domain of nNOS (Jaffrey and Snyder, 1996), shows no interaction with CAPON.

PDZ domains typically interact with a characteristic C-terminal motif in other proteins (Songyang et al., 1997). By contrast, the nNOS PDZ domain binds directly to other PDZ domains, such as those in PSD95, but has not previously been reported to interact with any known physiological C-terminal peptide motifs. Since we could not detect any PDZ domain motifs in the CAPON sequence we sought to determine the region in CAPON which accounted for nNOS binding. We investigated the domain of CAPON that interacts with nNOS using GST-CAPON fusion proteins containing various deletions at the C-terminus FIG. 4B). Immobilized fusion proteins were incubated with HEK 293 lysates containing nNOS. Bound nNOS was detected by Western blot. Robust interactions with nNOS are evident with constructs containing as little as the C-terminal thirteen amino acids of CAPON. Deleting the C-terminal 20 amino acids of CAPON abolishes its interactions with nNOS. These data show that the C-terminal portion of CAPON is necessary and sufficient for nNOS binding.

Recently Cantley and associates (Songyang et al., 1997) identified consensus sequences for binding to several PDZ domains. Binding of PDZ ligands involves the C-terminus of proteins, with determinants of specificity lying within the eight or fewer C-terminal amino acids. A consistent requirement among all the PDZ domain ligands is a hydrophobic residue, such as valine or leucine, as the final amino acid. To determine if the binding of CAPON to nNOS exhibits similar sequence-specificity, we examined the binding of mutagenized His$_6$-CAPON fusion proteins to immobilized GST-nNOS PDZ domain fusion proteins (FIG. 4C). The C-terminal residue of CAPON is a valine, and conversion of this residue to alanine abolishes binding. Binding is also greatly reduced by changing the penultimate amino acid from alanine to aspartate. However, changing the n-2 amino acid from isoleucine to serine or alanine does not alter binding. These experiments indicate that the nNOS-CAPON interaction resembles those of other PDZ-C-terminal peptide ligand interactions. Specifically, C-terminal residues of CAPON are important for the specificity in CAPON binding to nNOS.

EXAMPLE 3.

CAPON and PSD95 Compete for Binding to nNOS

Figure 5A:
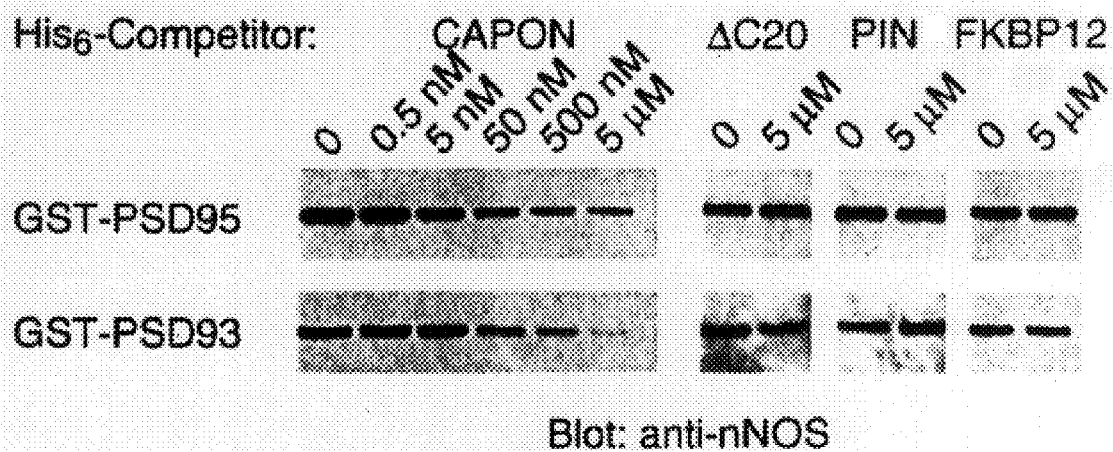
FIGS. 5A and 5B. CAPON and PSD95 compete for binding to nNOS.
Figure 5B:
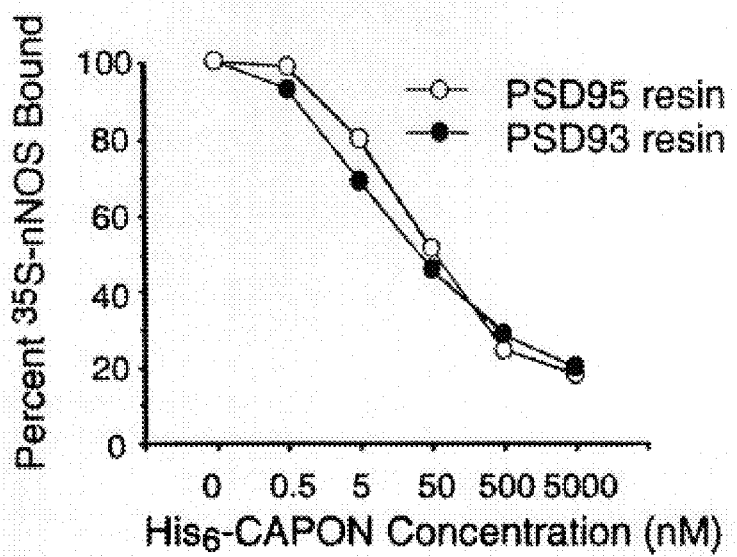

Since the nNOS PDZ domain is capable of both PDZ-PDZ interactions and PDZ-C-terminal peptide interactions we wondered whether CAPON and PSD95 can bind simultaneously to nNOS or whether their interactions with nNOS are mutually exclusive. To answer this question we incubated lysates of HEK-293 cells containing nNOS with various concentrations of a His$_6$-CAPON fusion protein, comprising the last 125 amino acids of CAPON, and then added these lysates to GST-PSD95 immobilized on glutathione agarose resin (FIG. 5A). After extensive washing of the resin, we assayed for nNOS bound to PSD95 by Western blot. As little as 5 nM His$_6$-CAPON causes a substantial reduction of nNOS binding to GST-PSD95. Half maximal reduction of binding is evident between 5 and 50 nM His$_6$-CAPON (FIG. 5B). Deletion of the C-terminal 20 amino acids of CAPON abolishes its ability to serve as a competitor for nNOS binding to GST-PSD95. As controls, we examined the effects of 5 μM His$_6$-PIN or 5 mM His$_6$-FK506 binding protein-12 kD (FKBP). Neither of these proteins compete for binding to nTNOS. nNOS also binds to the second PDZ domain of PSD93, a protein which is highly homologous to PSD95 (Brenman et al., 1996). His$_6$-CAPON is an effective competitor for nNOS binding to immobilized GST-PSD93 as well (FIG. 5A, B). These effects of CAPON likely reflect its binding to nNOS rather than to the PDZ domains of either PSD95 or PSD93 because CAPON fails to interact with either PSD93 or PSD95 using (i) a two-hybrid assay (see FIG. 1A) and (ii) in vitro experiments utilizing immobilized GST-PSD95 and purified recombinant CAPON (data not shown).

We wanted to determine if CAPON and PSD95 compete for binding to nNOS in intact cells. Accordingly, we transfected HEK-293 cells with various mixtures of expression plasmids containing cDNAs of hemagglutinin antigen (HA)-tagged nNOS, myc-tagged PSD95 and/or full-length CAPON. Following immunoprecipitation with antibodies to HA, we examined which proteins coprecipitated. In cells expressing HA-nNOS and myc-PSD95, antibodies to HA coprecipitate myc-PSD95 (FIG. 6). When various amounts of CAPON cDNA containing expression plasmids are also transfected, HA-immunoprecipitates contain CAPON but substantially less PSD95.

Immunoprecipitations

Immunoprecipitations were performed by homogenizing one rat cerebellum in 3 ml lysis buffer followed by centrifugation at 100,000×g for 30 min at 4° C. Two hundred microliters of the supernatant was incubated with 40 ml of protein A-agarose (Oncogene Sciences, Cambridge, Mass.) and 5 mg of the indicated antibody for 60 min at 4° C. The resins were then washed with IP wash buffer (50 mM Tris-HCl (pH 7.7), 400 mM NaCl, and 2 mM EDTA) six times and eluted in 60 ul of 1×SDS-PAGE sample buffer by boiling. Western blots were performed using an nNOS-specific monoclonal antibody (Transduction Labs) or a PKC- b I/II monoclonal antibody (Santa Cruz Biotechnology, Inc., Santa Cruz, Calif.). The immunoprecipitating antibodies used as controls were from Santa Cruz Biotechnology, Inc.

For experiments utilizing 2', 5', ADP sepharose (Pharmacia), tissues were prepared identically as for immunoprecipitations except mouse cerebella were used and the homogenization volume was 400 ml per cerebellum. Supernatants were incubated with 100 ul of affinity resin. Incubations and washes were performed identically as for immunoprecipitations. The generation of mice with a targetted deletion of nNOS has been described previously (Huang et al., 1993).

Immunohistochemistry

Adult Sprague-Dawley rats (200–250 gm) were obtained from Charles River and housed at the Johns Hopkins Animal Care Facility. A polyclonal antiserum to the C-terminal region of human nNOS (residues 1419–1433) was kindly provided by J. Spangenberg (IncStar, Stillwater, MN). The peroxidase Elite staining kit was from Vector Laboratories.

Anesthetized rats were perfused through the left ventricle with 50 ml of 0.9% NaCl followed by 500 ml 4% paraformaldehyde in 0.1 M phosphate buffer (PB), pH 7.4. The brains were removed, cut into saggital blocks, and postfixed in 4% paraformaldehyde in 0.1 M PB for 4 h at room temperature. Blocks were cryoprotected for 2 days at 4° C. in 50 mM sodium phosphate, pH 7.4/0.1 M NaCl/20% (vol./vol.) glycerol. Brain sections, 40 mm thick, were cut on a sliding microtome. Free-floating sections were incubated in PBS (10 mM, pH 7.4/0.19 M NaCl), containing 4% normal goat serum (Jackson Labs), and 0.2% Triton X-100 for 45 min, and then incubated overnight at 4° C. with the primary antiserum diluted 1:500 (CAPON) or 1:15,000 (nNOS) in phosphate buffered saline (PBS) containing 2% goat serum and 0.1% Triton X-100. Immunoreactivity was visualized with the Vectastain ABC Elite kit following the nickel-enhanced diaminobenzidine procedure. To test immunohistochemical specificity of the CAPON antiserum, the antiserum was incubated overnight with 13.5 mg/ml of the antigenic fusion protein before incubation with brain sections.

In Situ Hybridization

In situ hybridization used DNA oligonucleotide probes corresponding to amino acids 478–503. Probes were end-labelled with [a-$^{32}$P] dATP and terminal deoxynucleotidyl transferase to a specific activity of 800 mCi/mg and in situ hybridization was performed as described previously (Jaffrey et al., 1994). Non-specific hybridization was determined using the corresponding sense probe.

References

Altschul, S. F., Gish, W., Miller, W., Myers, E. W., and Lipman, D. J. (1990). Basic local alignment search tool. J Mol Biol 215, 403–10.

Bredt, D. S. (1996). Targeting nitric oxide to its targets. Proc Soc Exp Biol Med 211, 41–8.

Bredt, D. S., Ferris, C. D., and Snyder, S. H. (1992). Nitric oxide synthase regulatory sites. Phosphorylation by cyclic AMP-dependent protein kinase, protein kinase C, and calcium/calmodulin protein kinase; identification of flavin and calmodulin binding sites. J Biol Chem 267, 10976–81.

Bredt, D. S., Hwang, P. M., and Snyder, S. H. (1990). Localization of nitric oxide synthase indicating a neural role for nitric oxide. Nature 347, 768–70.

Bredt, D. S., and Snyder, S. H. (1990). Isolation of nitric oxide synthetase, a calmodulin-requiring enzyme. Proc Natl Acad Sci U S A 87, 682–5.

Bredt, D. S., and Snyder, S. H. (1989). Nitric oxide mediates glutamate-linked enhancement of cGMP levels in the cerebellum. Proc Natl Acad Sci U S A 86, 9030–3.

Brenman, J. E., Chao, D. S., Gee, S. H., McGee, A. W., Craven, S. E., Santillano, D. R., Wu, Z., Huang, F., xia, H., Peters, M. F., Froehner, S. C., and Bredt, D. S. (1996). Interaction of nitric oxide synthase with the postsynaptic density protein PSD-95 and alphal-syntrophin mediated by PDZ domains. Cell 84, 757–67.

Brenman, J. E., Christopherson, K. S., Craven, S. E., McGee, A. W., and Bredt, D. S. (1996). Cloning and characterization of postsynaptic density 93, a nitric oxide synthase interacting protein. J Neurosci 16, 7407–15.

Cho, K. O., Hunt, C. A., and Kennedy, M. B. (1992). The rat brain postsynaptic density fraction contains a homolog of the Drosophila discs-large tumor suppressor protein. Neuron 9, 929–42.

Cohen, N. A., Brenman, J. E., Snyder, S. H., and Bredt, D. S. (1996). Binding of the inward rectifier K+channel Kir 2.3 to PSD-95 is regulated by protein kinase A phosphorylation. Neuron 17, 759–67.

Dawson, V. L., and Dawson, T. M. (1996). Nitric oxide in neuronal degeneration. Proc Soc Exp Biol Med 211, 33–40.

Dinerman, J. L., Dawson, T. M., Schell, M. J., Snowman, A., and Snyder, S. H. (1994). Endothelial nitric oxide synthase localized to hippocampal pyramidal cells: implications for synaptic plasticity. Proc Natl Acad Sci U S A 91, 4214–8.

Doyle, D. A., Lee, A., Lewis, J., Kim, E., Sheng, M., and MacKinnon, R. (1996). Crystal structures of a complexed and peptide-free membrane protein-binding domain: molecular basis of peptide recognition by PDZ. Cell 85, 1067–76.

Garthwaite, J., Garthwaite, G., Palmer, R. M. J., and Moncada, S. (1989). NMDA receptor activation induces nitric oxide synthesis from arginine in rat brain slices. Eur. J. Pharmacol. 172, 413–416.

Hecker, M., Mulsch, A., and Busse, R. (1994). Subcellular localization and characterization of neuronal nitric oxide synthase. J Neurochem 62, 1524–9.

Huang, E. P. (1997). Synaptic plasticity: a role for nitric oxide in LTP. Curr Biol 7.

Huang, P. L., Dawson, T. M., Bredt, D. S., Snyder, S. H., and Fishman, M. C. (1993). Targeted disruption of the neuronal nitric oxide synthase gene. Cell 75, 1273–86.

Huang, Z., Huang, P. L., Panahian, N., Dalkara, T., Fishman, M. C., and Moskowitz, M. A. (1994). Effects of cerebral ischemia in rnice deficient in neuronal nitric oxide synthase. Science 265, 1883–5.

Jaffrey, S. R., Cohen, N. A., Rouault, T. A., Klausner, R. D., and Snyder, S. H. (1994). The iron-responsive element binding protein: a target for synaptic actions of nitric oxide. Proc Natl Acad Sci U S A 91, 12994–8.

Jaffrey, S. R., and Snyder, S. H. (1996). PIN: an associated protein inhibitor of neuronal nitric oxide synthase. Science 274, 774–7.

Kavanaugh, W. M., and Williams, L. T. (1994). An alternative to SH2 domains for binding tyrosine-phosphorylated proteins. Science 266, 1862–5.

Kistner, U., Wenzel, B. M., Veh, R. W., Cases-Langhoff, C., Garner, A. M., Appeltauer, U., Voss, B., Gundelfinger, E. D., and Garner, C. C. (1993). SAP90, a rat presynaptic protein related to the product of the Drosophila tumor suppressor gene dlg-A. Journal of Biological Chemistry 268, 4580–4583.

Kornau, H.-C., Seeburg, P. H., and Kennedy, M. B. (1997). Interactions of ion channels and receptors with PDZ domain proteins. Current Opinion in Neurobiology 7, 368–373.

Kornau, H. C., Schenker, L. T., Kennedy, M. B., and Seeburg, P. H. (1995). Domain interaction between NMDA receptor subunits and the postsynaptic density protein PSD-95. Science 269, 1737–40.

Kozak, M. (1991). Structural features in eukaryotic mRNAs that modulate the initiation of translation. J Biol Chem 266, 19867–70.

Lennon, G., Auffray, C., M., P., and Soares, M. B. (1996). The I.M.A.G.E. consortium: An integrated analysis of genomes and their expression. Genomics 33, 151–52.

Li, X. J., Li, S. H., Sharp, A. H., Nucifora, F. J., Schilling, G., Lanahan, A., Worley, P., Snyder, S. H., and Ross, C. A. (1995). A huntingtin-associated protein enriched in brain with implications for pathology. Nature 378, 398–402.

Lipton, S. A., and Stamler, J. S. (1994). Actions of redox-related congeners of nitric oxide at the NMDA receptor. Neuropharmacology 33, 1229–33.

Moncada, S. (1994). Nitric oxide. J Hypertens Suppl 12, S35–9.

O'Dell, T. J., Huang, P. L., Dawson, T. M., Dinerman, J. L., Snyder, S. H., Kandel, E. R., and Fishman, M. C. (1994). Endothelial NOS and the blockade of LTP by NOS inhibitors in mice lacking neuronal NOS. Science 265, 542–6.

Ponting, C. P., and Phillips, C. (1995). DHR domains in syntrophins, neuronal NO synthases and other intracellular proteins. Trends Biochem Sci 20, 102–3.

Rodrigo, J., Springall, D. R., Uttenthal, O., Bentura, M. L., Abadia, M. F., Riveros, M. V., Martinez, M. R., Polak, J. M., and Moncada, S. (1994). Localization of nitric oxide synthase in the adult rat brain. Philos Trans R Soc Lond B Biol Sci 345, 175–221.

Ross, C. A. (1995). When more is less: pathogenesis of glutamine repeat neurodegenerative diseases. Neuron 15, 493–6.

Schuman, E. M., and Madison, D. V. (1994). Nitric oxide and synaptic function. Annu Rev Neurosci 17, 153–83.

Smith, D. B., and Johnson, K. S. (1988). Single-step purification of polypeptides expressed in Escherichia coli as fusions with glutathione S-transferase. Gene 67, 31–40.

Songyang, Z., Fanning, A. S., Fu, C., Xu, J., Marfatia, S. M., Chishti, A. H., Crompton, A., Chan, A. C., Anderson, J. M., and Cantley, L. C. (1997). Recognition of unique carboxyl-terminal motifs by distinct PDZ domains. Science 275, 73–7.

Stricker, N. L., Christopherson, K. S., Yi, B. A., Schatz, P. J., Raab, R. W., Dawes, G., Bassett, D. J., Bredt, D. S., and Li, M. (1997). PDZ domain of neuronal nitric oxide synthase recognizes novel C-terminal peptide sequences. Nat Biotechnol 15, 336–42.

van der Geer, P., and Pawson, T. (1995). The PTB domain: a new protein module implicated in signal transduction. Trends Biochem Sci 20, 277–80.

Yun, H. Y., Dawson, V. L., and Dawson, T. M. (1996). Neurobiology of nitric oxide. Crit Rev Neurobiol 10, 291–316.

Zhong, W., Feder, J. N., Jiang, M. M., Jan, L. Y., and Jan, Y. N. (1996). Asymmetric localization of a mammalian numb homolog during mouse cortical neurogenesis. Neuron 17, 43–53.

Zhou, M. M., Ravichandran, K. S., Olejniczak, E. F., Petros, A. M., Meadows, R. P., Sattler, M., Harlan, J. E., Wade, W. S., Burakoff, S. J., and Fesik S. W. (1995). Structure and ligand recognition of the phosphotyrosine binding domain of Shc. Nature 378, 584–92.

SEQUENCE LISTING SUMMARY

SEQ ID NO: 1. Rat capon cDNA
SEQ ID NO: 2. Rat capon amino acids
SEQ ID NO: 3. Human capon cDNA
SEQ ID NO: 4. Human capon amino acids
SEQ ID NO: 5. Rat nNOS amino acids
SEQ ID NO: 6. Human nNOS amino acids
SEQ ID NO: 7. nNOS probe
SEQ ID NO: 8. nNOS probe

What is claimed is:

1. An isolated rat Capon protein as shown in SEQ ID NO:2 which binds to the PDZ domain of a mammalian nitric oxide synthase (nNOS).

2. The Capon protein of claim 1 which is made by isolating the protein from rat cells.

3. The Capon protein of claim 1 which is produced recombinantly.

4. The Capon protein of claim 1 which is produced by synthetic chemical methods.

5. A fusion protein which comprises a first protein segment and a second protein segment fused to each other by means of a peptide bond, wherein the first protein segment comprises at least eight contiguous amino acids selected from the amino acid sequence shown in SEQ ID NO:2 or 4.

6. The fusion protein of claim 5 wherein the second protein segment comprises glutathione-S-transferase.

7. The fusion protein of claim 5 wherein the first protein segment comprises at least nine contiguous amino acids selected from the amino acid sequence shown in SEQ ID NO:2 or 4.

8. The fusion protein of claim 5 wherein the first protein segment comprises at least ten contiguous amino acids selected from the amino acid sequence shown in SEQ ID NO:2 or 4.

9. The fusion protein of claim 5 wherein the first protein segment comprises at least twelve contiguous amino acids selected from the amino acid sequence shown in SEQ ID NO:2 or 4.

10. The fusion protein of claim 5 wherein the first protein segment comprises at least twelve contiguous amino acids selected from the amino acid sequence shown in SEQ ID NO:2 or 4.

11. The fusion protein of claim 5 wherein the first protein segment comprises at least sixteen contiguous amino acids selected from the amino acid sequence shown in SEQ ID NO:2 or 4.

12. An isolated fragment of Capon comprising at least eight contiguous amino acids as shown in SEQ ID NO:2 or 4, wherein the fragment binds to a PDZ domain of a mammalian neuronal nitric oxide synthase (nNOS).

13. The isolated fragment of claim 12, which comprises at least nine contiguous anilino acids of Capon.

14. The isolated fragment of claim 12, which comprises at least ten contiguous amino acids of Capon.

15. The isolated fragment of claim 12, which comprises at least twelve contiguous amino acids of Capon.

16. The isolated fragment of claim 12, which comprises at least thirteen contiguous amino acids of Capon.

17. The isolated fragment of claim 12, which comprises at least sixteen contiguous amino acids of Capon.

18. An isolated fragment of Capon comprising at least 8 contiguous amino acids as shown in SEQ ID NO:4, wherein the isolated fragment binds to a PDZ domain of a human neuronal nitric oxide synthase (nNOS).

19. The isolated fragment of claim 18, which comprises at least nine contiguous amino acids of Capon.

20. The isolated fragment of claim 18, which comprises at least ten contiguous amino acids of Capon.

21. The isolated fragment of claim 18, which comprises at least twelve contiguous amino acids of Capon.

22. The isolated fragment of claim 18, which comprises at least thirteen contiguous amino acids of Capon.

23. The isolated fragment of claim 18, which comprises at least sixteen contiguous amino acids of Capon.

* * * * *

UNITED STATES PATENT AND TRADEMARK OFFICE
CERTIFICATE OF CORRECTION

PATENT NO.: 6,103,872

DATED: August 15, 2000

INVENTORS: Solomon H. SNYDER, et al.

It is certified that errors appear in the above-identified patent and that said Letters Patent is hereby corrected as shown below:

On the cover page, right column, line 3, "Asociated" has been deleted and in its place --Associated-- has been inserted.

line 20, "NNOS" has been deleted and in its place --nNOS-- has been inserted.

Claim 5, column 45, line 66, "segnent" has been deleted and in its place --segment-- has been inserted.

Claim 10, column 47, line 6, "twelve" has been deleted and in its place --thirteen-- has been inserted.

Claim 13, column 47, line 18, "anilino" has been deleted and in its place --amino-- has been inserted.

Signed and Sealed this

Twenty-fourth Day of April, 2001

Attest:

NICHOLAS P. GODICI

Attesting Officer

Acting Director of the United States Patent and Trademark Office